United States Patent
Wakamiya

(10) Patent No.: US 10,514,376 B2
(45) Date of Patent: Dec. 24, 2019

(54) POSITION ADJUSTMENT METHOD FOR MOVABLE UNIT IN SAMPLE ANALYZER, AND SAMPLE ANALYZER

(71) Applicant: SYSMEX CORPORATION, Kobe-shi, Hyogo (JP)

(72) Inventor: Yuji Wakamiya, Kobe (JP)

(73) Assignee: SYSMEX CORPORATION, Kobe-shi (JP)

( * ) Notice: Subject to any disclaimer, the term of this patent is extended or adjusted under 35 U.S.C. 154(b) by 725 days.

(21) Appl. No.: 14/011,422

(22) Filed: Aug. 27, 2013

(65) Prior Publication Data

US 2013/0344622 A1  Dec. 26, 2013

Related U.S. Application Data

(63) Continuation-in-part of application No. PCT/JP2012/054716, filed on Feb. 27, 2012.

(30) Foreign Application Priority Data

Feb. 28, 2011 (JP) ................. 2011-042571

(51) Int. Cl.
*C12Q 1/68* (2018.01)
*G01N 35/10* (2006.01)
(Continued)

(52) U.S. Cl.
CPC ......... *G01N 33/53* (2013.01); *G01N 35/1011* (2013.01); *G01N 35/00871* (2013.01);
(Continued)

(58) Field of Classification Search
CPC ......... G01N 35/1011; G01N 35/00871; G01N 2035/0091; G01N 2035/0491
See application file for complete search history.

(56) References Cited

U.S. PATENT DOCUMENTS 5,104,621 A  4/1992 Pfost et al.
6,584,430 B1  6/2003 Rosenbaum et al.
(Continued)

FOREIGN PATENT DOCUMENTS

EP  2098871 A2  9/2009
EP  2098871 A3  8/2017
(Continued)

OTHER PUBLICATIONS

Nippon Denshi Datum Kabushiki Kaisha, "Seihin Shokai High Speed, Micro Volume Technology ga Rinsho Kensa o Kaemasu", Jeol Analytical News, Apr. 2003, pp. 6, No. 55.
(Continued)

*Primary Examiner* — Kathryn Wright
(74) *Attorney, Agent, or Firm* — Metrolex IP Law Group, PLLC

(57) ABSTRACT

A position adjustment method for a movable unit in a sample analyzer which includes: a measurement section which causes a movable unit to operate in order to measure a sample; and a communication section for performing communication with outside, includes: a terminal screen displaying step of causing a portable terminal device to display a position adjustment screen for accepting an input for changing a position of the movable unit, the portable terminal device configured to be able to perform communication with the communication section; and a movement executing step of causing the measurement section to execute a movement of a corresponding movable unit in accordance with the input for changing the position received by the communication section.

18 Claims, 12 Drawing Sheets

(51) Int. Cl.
*G01N 33/53* (2006.01)
*G01N 35/00* (2006.01)
*G01N 35/04* (2006.01)

(52) U.S. Cl.
CPC ........... *G01N 2035/0091* (2013.01); *G01N 2035/0491* (2013.01)

(56) References Cited

U.S. PATENT DOCUMENTS

| | | | |
|---|---|---|---|
| 2002/0095974 A1 | 7/2002 | Gilson et al. | |
| 2006/0046299 A1* | 3/2006 | Nishikiori | G05B 15/02 436/43 |
| 2006/0051246 A1* | 3/2006 | Toi | G01N 35/1011 422/561 |
| 2011/0077752 A1* | 3/2011 | Hamada | G05B 15/02 700/73 |
| 2011/0160909 A1* | 6/2011 | Glauser | G01N 35/00722 700/264 |
| 2015/0029331 A1* | 1/2015 | Ha | G01N 35/00594 348/95 |

FOREIGN PATENT DOCUMENTS

| | | | | |
|---|---|---|---|---|
| JP | 07-114439 A | 5/1995 | | |
| JP | 2001-091522 A | 4/2001 | | |
| JP | 2004-200708 A | 7/2004 | | |
| JP | 2005-134217 A | 5/2005 | | |
| JP | 2008-102644 A | 5/2008 | | |
| WO | WO-2009130318 A2 * | 10/2009 | ....... | G01N 35/00722 |

OTHER PUBLICATIONS

Nippon Denshi Datum Kabushiki Kaisha, "Seihin Shokai High Speed, Micro Volume Technology ga Rinsho Kensa o Kaemasu", Jeol Analytical News, Apr. 2004, pp. 6, No. 55.

* cited by examiner

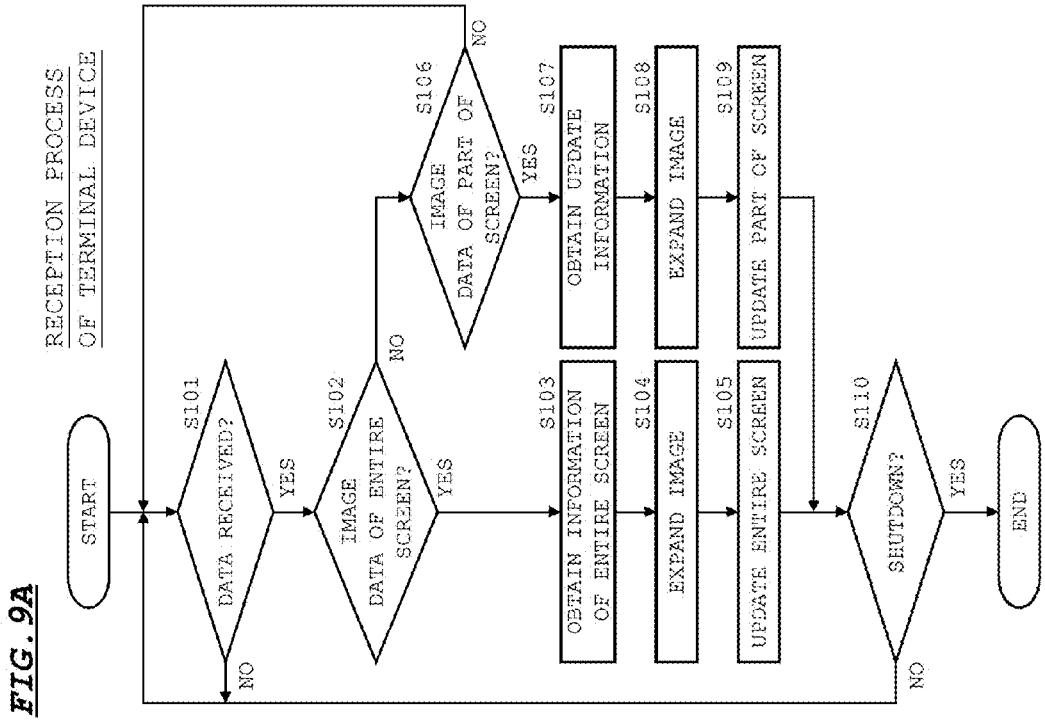

POSITION ADJUSTMENT METHOD FOR MOVABLE UNIT IN SAMPLE ANALYZER, AND SAMPLE ANALYZER

CROSS REFERENCE TO RELATED APPLICATION

This application is a continuation of International Application No. PCT/JP2012/054716 filed on Feb. 27, 2012, entitled "POSITION ADJUSTMENT METHOD FOR MOVABLE UNIT IN SAMPLE ANALYZER, AND SAMPLE ANALYZER", which claims priority under 35 U.S.C. Section 119 of Japanese Patent Application No. 2011-042571 filed on Feb. 28, 2011, entitled "POSITION ADJUSTMENT METHOD FOR PROCESSING UNIT IN SAMPLE ANALYZER, AND SAMPLE ANALYZER". The disclosure of the above application is incorporated herein by reference.

BACKGROUND OF THE INVENTION

1. Field of the Invention

The present invention relates to a position adjustment method for movable units in a sample analyzer which causes movable units to operate in order to perform measurement, and to the sample analyzer.

2. Disclosure of Related Art

To date, there are known analyzers that move mechanism sections to predetermined positions to perform measurements. For example, there has been proposed an analyzer including a sampling needle which aspirates a specimen from a specimen container at a predetermined position, an injection part into which a specimen aspirated by the sampling needle is discharged, and a control section which controls the sampling needle.

The sampling needle aspirates a specimen from a specimen container, moves to the position of the injection part, and discharges the aspirated specimen into the injection part. Since a visible mark is provided at a center portion of the injection part, the position of the sampling needle can be adjusted by performing a key operation with reference to this mark.

With the analyzer above, in a case where the place at which to perform a key operation and the location on which to perform position adjustment are away from each other, an operator cannot perform the key operation and confirmation of the position adjustment simultaneously. Accordingly, after performing the key operation, the operator has to confirm whether a relevant mechanism section is at a predetermined position, which results in troublesome adjustment work.

SUMMARY OF THE INVENTION

A first aspect of the present invention relates to a position adjustment method for a movable unit in a sample analyzer which includes: a measurement section having a movable unit and configured to perform a measurement of a sample with actuating the movable unit; and a communication section configured to communicate with outside, the position adjustment method comprising: a terminal screen displaying step of causing a portable terminal device to display a position adjustment screen for accepting an input for changing a position of the movable unit, the portable terminal device configured to be able to perform communication with the communication section; an inputting step of performing the input for changing the position onto the position adjustment screen; a transmitting step of transmitting the input for changing the position performed onto the position adjustment screen, from the terminal device to the communication section; and a movement executing step of causing the measurement section to execute a movement of the corresponding movable unit in accordance with the input for changing the position received by the communication section.

According to the position adjustment method for the movable unit in the sample analyzer according to this aspect, even when the movable unit is away from the position at which to operate the sample analyzer, by bringing the terminal device near the movable unit, it is possible to give instruction to change the position of the movable unit via the position adjustment screen displayed in the terminal device, while viewing the position of the movable unit. Therefore, when performing position adjustment of the movable unit, an operator need not come and go between the position at which to operate the sample analyzer and the movable unit, and can perform position adjustment of the movable unit very simply.

A second aspect of the present invention relates to a sample analyzer. The sample analyzer according to this aspect includes: a measurement section having a movable unit, configured to perform a measurement of a sample by actuating the movable unit; a communication section configured to communicate with outside; and a controller, wherein the controller causes a portable terminal device to display a position adjustment screen for accepting an input for changing a position of the movable unit, the portable terminal device configured to be able to perform communication with the communication section, and causes, upon receiving via the communication section an input for changing the position onto the position adjustment screen, the measurement section to execute a movement of the movable unit in accordance with the input.

In the sample analyzer according to this aspect, effects similar to those of the position adjustment method for a movable unit in the sample analyzer according to the first aspect above can be obtained.

BRIEF DESCRIPTION OF THE DRAWINGS

The above and other objects and new features of the present invention will be fully clarified by the following description of the embodiment, when read in conjunction with the accompanying drawings.

FIGS. 9A and 9B show flow charts of a reception process and a transmission process performed by a terminal device according to an embodiment;

Figure 1:
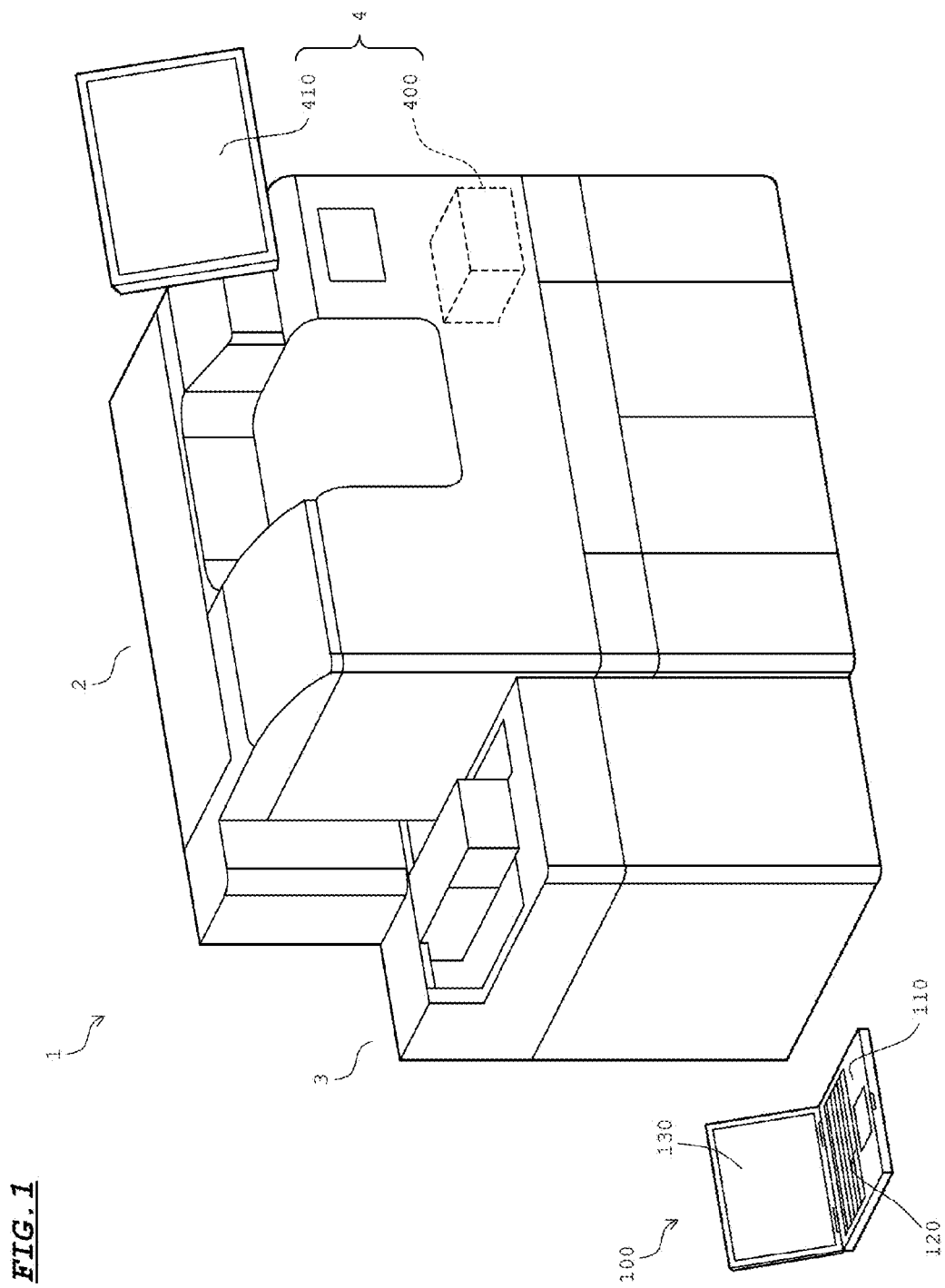
FIG. 1 is a perspective view showing an overall configuration of an immunoanalyzer according to an embodiment.

It should be noted that the drawings are solely for description and do not limit the scope of the present invention by any degree.

DESCRIPTION OF THE PREFERRED EMBODIMENTS

The present embodiment is realized by applying the present invention to an immunoanalyzer for performing tests for various items such as hepatitis B, hepatitis C, tumor marker, and thyroid hormone, using a sample such as blood.

In the present embodiment, an immunoanalyzer 1 corresponds to a "sample analyzer" described in claims. A measurement mechanism section 2 corresponds to a "measurement section" described in claims. A control device 4 corresponds to a "controller" described in claims. A sample dispensing arm 5, an R1 reagent dispensing arm 6, an R2 reagent dispensing arm 7, and an R3 reagent dispensing arm 8 correspond to a "movable unit" described in claims. A battery backup RAM 204 corresponds to a "storage section" described in claims. A RAM 403 corresponds to the "storage section" described in claims. A communication interface 408 corresponds to a "communication section" described in claims. A display input section 410 corresponds to a "display section" described in claims. A position adjustment main screen 500 corresponds to a "position adjustment screen" described in claims. A set value display region 510 corresponds to a "selection accepting screen" described in claims. A coarse adjustment display region 522 corresponds to a "position adjustment screen" described in claims. A fine adjustment screen 600 corresponds to a "position adjustment screen" described in claims. Movement buttons 621b, 621c, 631b to 634b, 631c to 634c, 641b, and 641c correspond to a "movement key" and a "button" described in claims. A confirmation button 672 corresponds to an "operation confirmation button" described in claims. A set value display region 510 corresponds to a "first display region" described in claims. An adjustment location display region 521 corresponds to a "second display region" described in claims. A coarse adjustment display region 522 corresponds to a "third display region" described in claims. A pulse movement value display region 610 corresponds to a "movement amount setting section" described in claims. However, the correspondence between the claims and the present embodiment is merely an example, and does not limit the claims to the present embodiment.

Hereinafter, the immunoanalyzer according to the present embodiment will be described with reference to the drawings.

FIG. 1 is a perspective view showing an overall configuration of an immunoanalyzer 1. The immunoanalyzer 1 includes a measurement mechanism section 2, a sample transporting section (sampler) 3, and a control device 4. The measurement mechanism section 2 is communicably connected to the sample transporting section 3 and the control device 4. The sample transporting section 3 is configured to be able to transport a rack in which a plurality of test tubes each containing a sample are placed. The control device 4 includes a body 400, and a display input section 410 implemented by a touch panel, and is capable of performing wireless communication with a terminal device 100. The terminal device 100 is used when performing position adjustment of various types of units in the measurement mechanism section 2, and includes a body 110, an input section 120, and a display section 130. Position adjustment performed in the measurement mechanism section 2 will be described later with reference to FIGS. 6 and 7.

Figure 2:
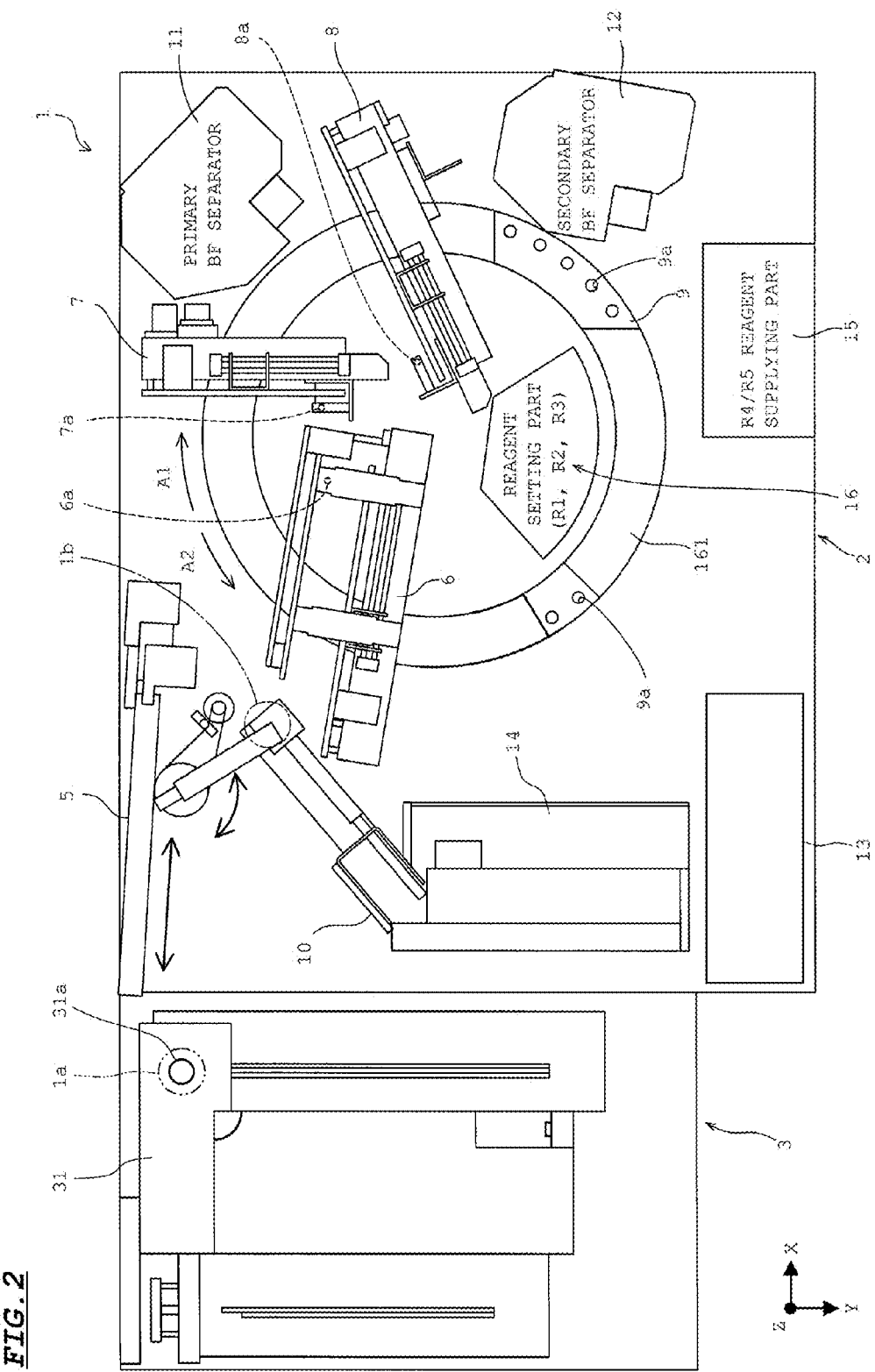
FIG. 2 is a plan view showing a configuration of the inside of an immunoanalyzer viewed from above according to an embodiment.

FIG. 2 is a plan view showing a configuration of the inside of the immunoanalyzer 1, viewed from above.

The measurement mechanism section 2 includes a sample dispensing arm 5, an R1 reagent dispensing arm 6, an R2 reagent dispensing arm 7, an R3 reagent dispensing arm 8, a reaction part 9, a cuvette supplying part 10, a primary BF separator 11, a secondary BF separator 12, a pipette tip supplying part 13, a detection part 14, an R4/R5 reagent supplying part 15, and a reagent setting part 16. The sample transporting section 3 is configured to be able to transport a rack in which a plurality of test tubes each containing an unprocessed sample are placed.

In the immunoanalyzer 1, a sample such as blood to be measured and a buffer solution (R1 reagent) are mixed together, and to the obtained mixture solution, a reagent (R2 reagent) is added which contains magnetic particles carrying a capture antibody to be bound to an antigen contained in the sample. By attracting magnetic particles carrying the capture antibody bound to the antigen, to a magnet (not shown) of the primary BF (Bound Free) separator 11, components in the sample that are not bound to the capture antibody are removed. Then, a labeled antibody (R3 reagent) is further added thereto, and magnetic particles carrying the capture antibody bound to the labeled antibody and the antigen are attracted to a magnet (not shown) of the secondary BF separator 12, whereby the R3 reagent containing the labeled antibody that is unreacted is removed. Further, a dispersion liquid (R4 reagent) and a luminescent substrate (R5 reagent) which emits light in a reaction process with the labeled antibody are added. Then, the amount of light generated in the reaction between the labeled antibody and the luminescent substrate is measured. Through this process, the antigen contained in the sample bound to the labeled antibody is quantitatively measured.

The cuvette supplying part 10 is configured to be able to accommodate a plurality of cuvettes, and sequentially supplies cuvettes one by one to a discharge position 1b for the sample dispensing arm 5.

As shown in FIG. 2, the R1 reagent dispensing arm 6 has a pipette 6a attached thereto for aspirating and discharging the R1 reagent. The R1 reagent dispensing arm 6 aspirates the R1 reagent set in the reagent setting part 16 by use of the pipette 6a, and dispenses (discharges) the aspirated R1 reagent into a cuvette placed at the discharge position 1b.

The pipette tip supplying part 13 transports one by one a plurality of pipette tips (not shown) that have been fed thereinto, to a tip attaching position (not shown) for the sample dispensing arm 5. Thereafter, the pipette tip is attached to the tip of the pipette of the sample dispensing arm 5 at the tip attaching position.

The sample dispensing arm 5 aspirates, by use of the attached pipette tip, the sample in a test tube transported to a sample aspiration position 1a by the sample transporting section 3. This aspiration is performed through a hole 31a formed in a top plate 31 which covers the transport path of the sample transporting section 3. The sample dispensing arm 5 dispenses (discharges) the aspirated sample into the cuvette at the discharge position 1b. In this cuvette, the R1 reagent has been dispensed in advance by the R1 reagent dispensing arm 6. Then, the cuvette is transferred to the reaction part 9 by means of a catcher not shown of the R1 reagent dispensing arm 6.

As shown in FIG. 2, the R2 reagent dispensing arm 7 has a pipette 7a attached thereto for aspirating and discharging the R2 reagent. The R2 reagent dispensing arm 7 aspirates the R2 reagent set in the reagent setting part 16 by use of the pipette 7a, and dispenses (discharges) the aspirated R2 reagent into the cuvette containing the R1 reagent and the sample.

As shown in FIG. 2, the reaction part 9 is formed in an annular shape so as to surround the reagent setting part 16 having a round shape. Further, the reaction part 9 includes a plurality of cuvette setting parts 9a arranged along the outline of the reaction part 9 at predetermined intervals. The cuvettes set in the cuvette setting part 9a are heated to about 42° C. Accordingly, the reaction between the sample and the various reagents in each cuvette is promoted. Further, the reaction part 9 is configured to be able to rotate in the clockwise direction (arrow A1 direction), and moves the respective cuvettes set in the cuvette setting parts 9a to their corresponding processing positions at which various types of processes (e.g., dispensing of a reagent) are performed.

Each cuvette containing a sample, the R1 reagent, and the R2 reagent is transferred from the reaction part 9 to the primary BF separator 11 by means of a catcher not shown. The primary BF separator 11 removes components in the sample that are not bound to the capture antibody, from the specimen in the cuvette.

As shown in FIG. 2, the R3 reagent dispensing arm 8 has a pipette 8a attached thereto for aspirating and discharging the R3 reagent. The R3 reagent dispensing arm 8 aspirates the R3 reagent set in the reagent setting part 16 by use of the pipette 8a. Further, the R3 reagent dispensing arm 8 dispenses (discharges), by use of the pipette 8a, the aspirated R3 reagent into the cuvette which has been transferred to the reaction part 9 from the primary BF separator 11.

The cuvette which contains the R3 reagent and the specimen after the removal process performed by the primary BF separator 11 is transferred from the reaction part 9 to the secondary BF separator 12 by means of a catcher not shown. The secondary BF separator 12 removes the R3 reagent containing the labeled antibody that is unreacted.

The R4/R5 reagent supplying part 15 sequentially dispenses, by means of a tube not shown, the R4 reagent and the R5 reagent into the cuvette containing the specimen after the removal process performed by the secondary BF separator 12.

The detection part 14 obtains, by means of a photo multiplier tube, light generated in the reaction process between the luminescent substrate and the labeled antibody bound to the antigen in the sample which has been subjected to predetermined processes, thereby measuring the amount of antigen contained in the sample.

Above the reagent setting part 16, a cover 161 having a round shape is arranged so as to cover both the reagent setting part 16 and the reaction part 9. At predetermined positions of the cover 161, openings through which the R1 to R3 reagent dispensing arms aspirate reagents, and openings through which the R1 to R3 reagent dispensing arms perform movement of cuvettes and dispensing processes are formed.

Figure 3:
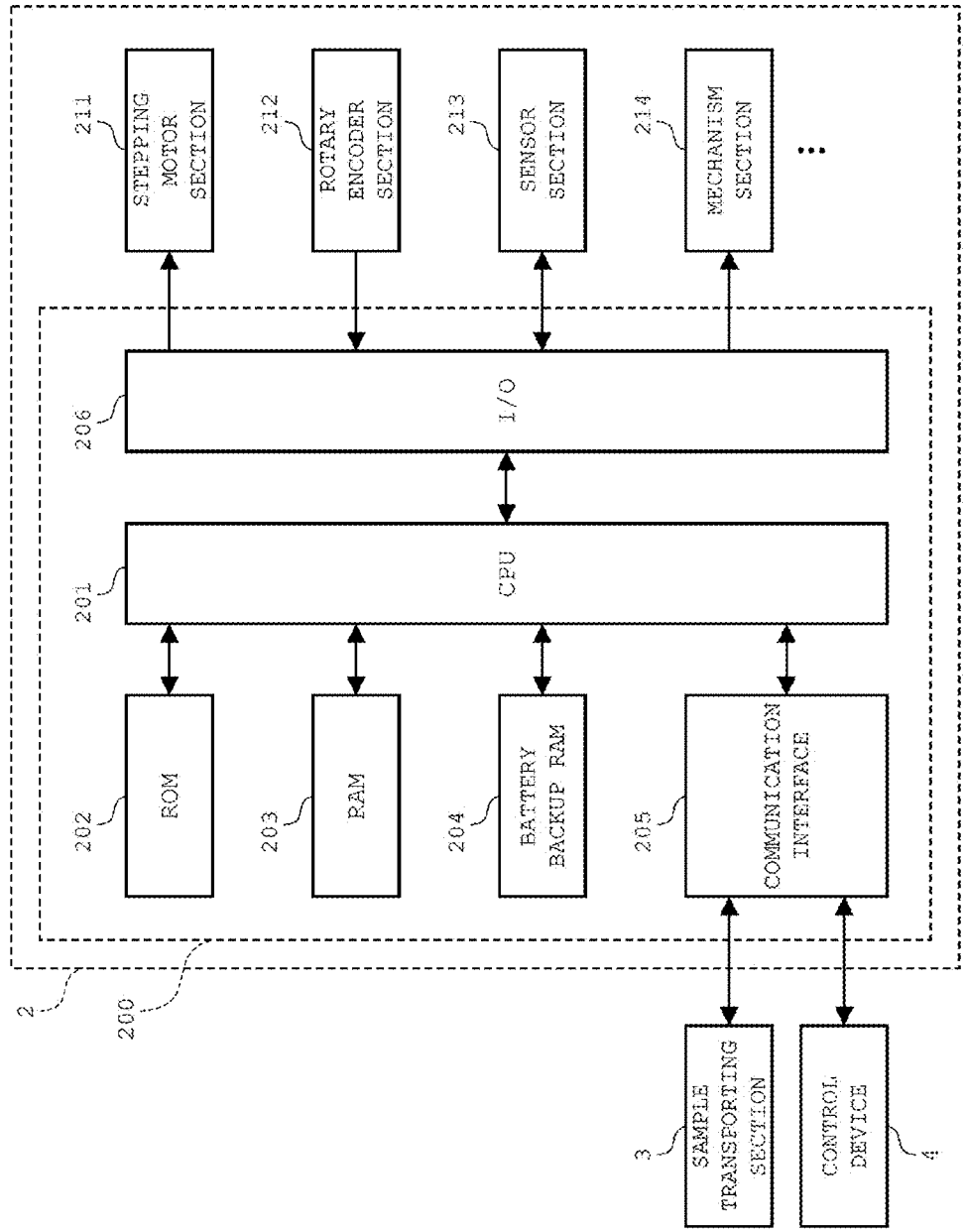
FIG. 3 shows a circuit configuration of a measurement mechanism section according to an embodiment.

FIG. 3 shows a circuit configuration of the measurement mechanism section 2.

The measurement mechanism section 2 includes a control section 200, a stepping motor section 211, a rotary encoder section 212, a sensor section 213, and a mechanism section 214. The control section 200 includes a CPU 201, a ROM 202, a RAM 203, a battery backup RAM 204, a communication interface 205, and an I/O interface 206.

The CPU 201 executes computer programs stored in the ROM 202 and computer programs loaded onto the RAM 203. The RAM 203 is used for reading out computer programs stored in the ROM 202, and is also used as a work area for the CPU 201 when the CPU 201 executes these computer programs.

The battery backup RAM 204 is configured such that stored contents are not deleted even when the power source of the measurement mechanism section 2 is turned off. In the battery backup RAM 204, set values of each unit in the measurement mechanism section 2 are stored. The set values will be described later with reference to FIG. 6.

The communication interface 205 is connected to the sample transporting section 3 and the control device 4. The CPU 201 transmits to the control device 4 optical information (data of the amount of light generated in the reaction between the labeled antibody and the luminescent substrate) of the sample, and receives signals from the control device 4, via the communication interface 205. Further, the CPU 201 transmits a drive instruction signal to the sample transporting section 3 via the communication interface 205.

The CPU 201 is connected to the stepping motor section 211, the rotary encoder section 212, the sensor section 213, and the mechanism section 214, via the I/O interface 206.

The stepping motor section 211 includes stepping motors for respectively driving the units for performing processes in the measurement mechanism section 2. Each stepping motor is controlled by the CPU 201 via the I/O interface 206.

The rotary encoder section 212 includes rotary encoders which respectively correspond to the stepping motors. Each rotary encoder outputs pulses by the number that corresponds to the amount of rotational displacement of its corresponding stepping motor. By counting the number of pulses outputted by each rotary encoder, the amount of rotation of its corresponding stepping motor can be detected. A detection signal of each rotary encoder is outputted to the CPU 201 via the I/O interface 206.

The sensor section 213 includes a plurality of sensors which detect that the respective units in the measurement mechanism section 2 are at predetermined positions. By means of detection signals from these sensors, it is possible to know at which positions the units in the measurement mechanism section 2 are positioned. Each sensor is controlled by the CPU 201 via the I/O interface 206. Further, a detection signal of each sensor is outputted to the CPU 201 via the I/O interface 206.

The mechanism section 214 includes other mechanisms included in the measurement mechanism section 2, and these mechanisms are controlled by the CPU 201 via the I/O interface 206.

Figure 4:
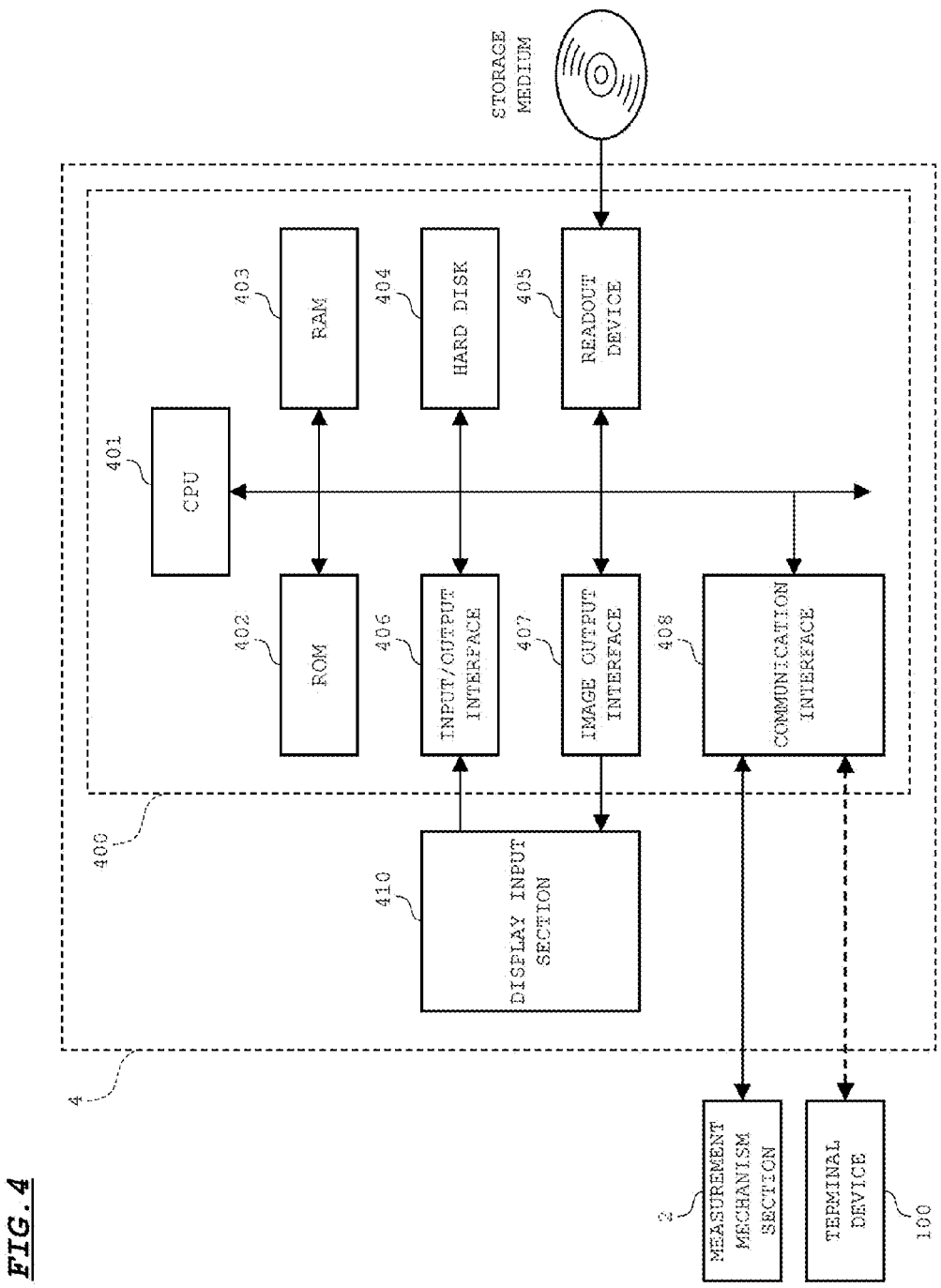
FIG. 4 shows a circuit configuration of a control device according to an embodiment.

FIG. 4 shows a circuit configuration of the control device 4.

The control device 4 is implemented by a personal computer, and includes the body 400 and the display input section 410. The body 400 includes a CPU 401, a ROM 402, a RAM 403, a hard disk 404, a readout device 405, an input/output interface 406, an image output interface 407, and a communication interface 408.

The CPU 401 executes computer programs stored in the ROM 402 and computer programs loaded onto the RAM 403. The RAM 403 is used for reading out computer programs stored in the ROM 402 and the hard disk 404. The RAM 403 is also used as a work area for the CPU 401 when the CPU 401 executes these computer programs.

In the hard disk 404, various computer programs, such as an operating system and application programs, to be executed by the CPU 401, and data used for execution of such computer programs are installed. That is, a program for displaying a position adjustment main screen 500 (see FIG. 6) and a fine adjustment screen 600 (see FIG. 7) for accepting a change of a set value of each unit in the measurement mechanism section 2 is installed. Moreover, a program for generating image data based on these screens, transmitting the generated image data to the terminal device 100, and rewriting a set value in accordance with a change of the set value received from the terminal device 100 is installed.

The readout device 405 is implemented by a CD drive, a DVD drive, or the like, and can read out computer programs and data stored in a storage medium.

The input/output interface 406 receives a signal outputted from the display input section 410. The image output interface 407 outputs a video signal corresponding to image data, to the display input section 410. The display input section 410 displays an image based on the video signal outputted from the image output interface 407, and outputs an instruction accepted from a user via the screen of the display input section 410, to the input/output interface 406.

When inputting a numerical value via the display input section 410, a key board image for accepting a numerical value input is displayed in the display input section 410. By pressing digits displayed on this image, the user can input a numerical value.

The communication interface 408 transmits signals on the body 400 side to the measurement mechanism section 2 and the terminal device 100, and receives signals transmitted from the measurement mechanism section 2 and the terminal device 100. The terminal device 100 and the communication interface 408 are connected to each other so as to be able to perform wireless communication with each other. In order to perform the wireless communication, the communication interface 408 includes a wireless LAN card as a communication module. The wireless LAN card is configured to be able to perform wireless communication with a communication interface 118 of the terminal device 100 via a wireless LAN router not shown. With this wireless LAN communication environment, physical layers in the wireless communication between the terminal device 100 and the control device 4 are constructed. Establishment of an upper layer communication channel is realized by transmitting and receiving IP packets using a TCP/IP protocol via the wireless LAN router as described later.

Figure 5:
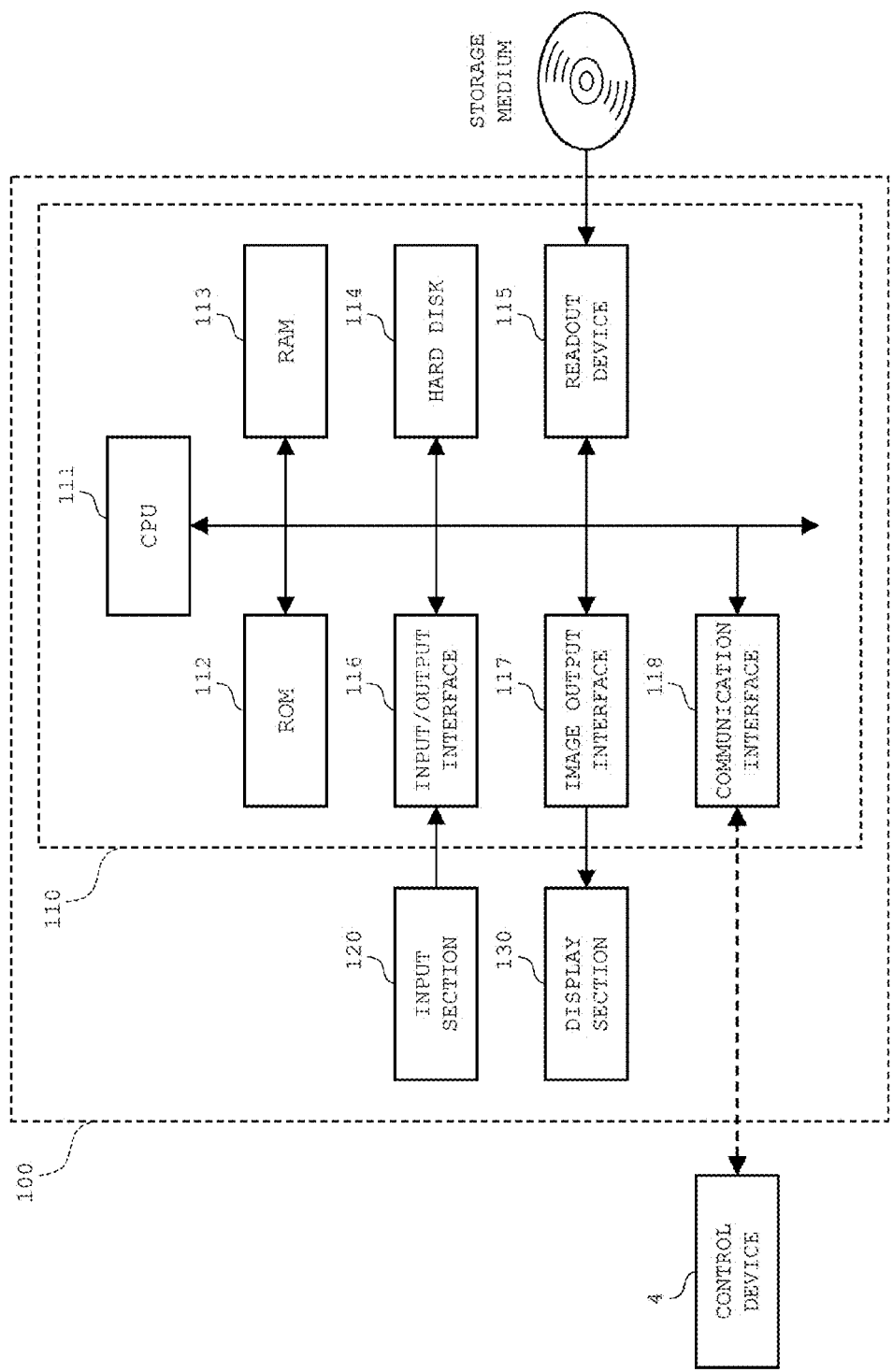
FIG. 5 shows a circuit configuration of a terminal device according to an embodiment.

FIG. 5 shows a circuit configuration of the terminal device 100.

The terminal device 100 is implemented by a notebook personal computer, and includes the body 110, the input section 120, and the display section 130. The body 110 includes a CPU 111, a ROM 112, a RAM 113, a hard disk 114, a readout device 115, an input/output interface 116, an image output interface 117, and the communication interface 118. Since the circuit configuration of the body 110 is substantially the same as the circuit configuration of the body 400 of the control device 4, description thereof is omitted here.

The input section 120 is implemented by a touch pad and a key board. By the user operating the input section 120, an input signal is sent from the input section 120 to the input/output interface 116. The display section 130 is implemented by a display, and displays an image in accordance with image data outputted from the image output interface 117.

The communication interface 118 transmits signals on the body 110 side to the control device 4 and receives signals transmitted from the control device 4. The control device 4 and the communication interface 118 are connected to each other so as to be able to perform wireless communication with each other. As in the case of the communication interface 408 of the control device 4, the communication interface 118 includes a wireless LAN card as a communication module for performing wireless communication.

In the hard disk 114, a program for displaying image data transmitted from the control device 4 and for transmitting a content inputted via the input section 120, to the control device 4 is installed. This program is not a dedicated program that controls position adjustments of the respective units in the measurement mechanism section 2 described later, but a general-purpose program for displaying received image and transmitting an inputted content.

In the present embodiment, for example, AIR of Adobe Systems Incorporated is installed as an execution environment, and applications executed in this execution environment can be installed. Programs executable in AIR are executable irrespective of the operating system as long as AIR is installed. Therefore, even if the operating system of the terminal device 100 is changed, it is not necessary to newly prepare programs to be executed in the terminal device 100.

Figure 6:
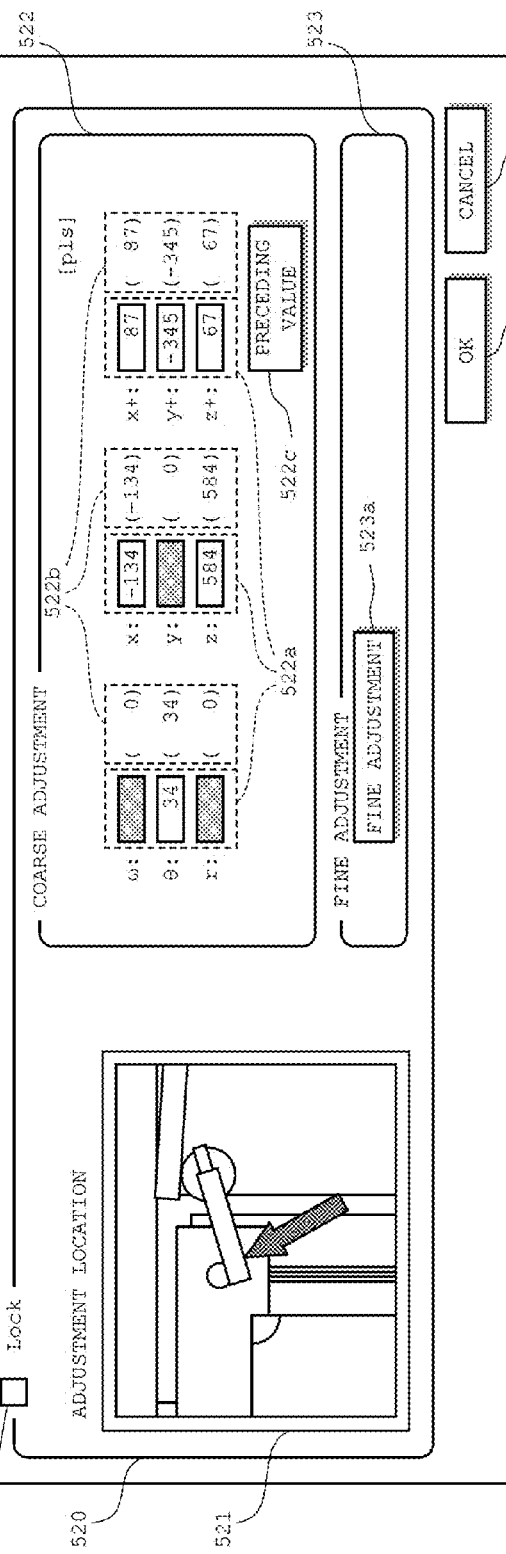
FIG. 6 shows a position adjustment main screen according to an embodiment.

FIG. 6 shows the position adjustment main screen 500 for performing position adjustment of each unit in the measurement mechanism section 2.

The position adjustment main screen 500 is displayed in a synchronized manner in the display input section 410 of the control device 4 and the display section 130 of the terminal device 100 as described later. Accordingly, the user can perform an operation onto the position adjustment main screen 500, via either the display input section 410 or the input section 120. It should be noted that when the position adjustment main screen 500 is displayed, the respective units in the measurement mechanism section 2 are all positioned at their origin positions.

The position adjustment main screen 500 includes a set value display region 510, a detail display region 520, an OK button 531, and a cancel button 532.

The set value display region 510 is a region in which operation positions of the respective units in the measurement mechanism section 2 are displayed. As shown in FIG. 6, the set value display region 510 includes a unit name item, an operation location item, and set value items ($\omega$, $\theta$, r, x, y, z, x+, y+, and z+). The unit name item indicates a unit name of each unit arranged in the measurement mechanism section 2, and the operation location item indicates an operation position of each unit. Each set value item defines a moved position of the unit relative to its operation position as a specific numerical value (the number of pulses). That is, an origin position has been set for each unit, and each set value is the number of pulses to be outputted to a corresponding stepping motor in order to drive the unit from its origin position to its moved position.

x, y, and z represent the numbers of pulses for driving a unit in the coordinate axes X, Y, and Z directions (see FIG. 2), respectively, which are set in the measurement mechanism section 2. θ represents the number of pulses for rotating a unit about the Z axis. ω represents, in a case where an operation location of a unit corresponds to a part of another mechanism that is rotatable about the Z axis, the number of pulses for rotating said another mechanism (hereinafter referred to as "receiving-side mechanism") about the Z axis. r represents, in a unit that expands and contracts, the number of pulses for driving the unit in the expanding/contracting direction. x+, y+, and z+ represent offset amounts of the set values x, y, and z, respectively. It should be noted that, among the set values of each operation location, the value of a set value item not used in defining a moved position of the corresponding unit is set to be 0.

When any one of operation location items is pressed (selected) by the user, the line of this operation location item is displayed in a reversed manner. FIG. 6 shows a state where the operation location "2: sampler aspiration position" of "sample arm" is displayed in a reversed manner. It should be noted that "2: sampler aspiration position" corresponds to the sample aspiration position 1*a* in FIG. 2.

The value of each set value item is stored in the battery backup RAM 204 of the measurement mechanism section 2, associated with its corresponding unit name item and operation location item. When display of the position adjustment main screen 500 is started, these pieces of information are read from the battery backup RAM 204, and the set value display region 510 is displayed as shown in FIG. 6.

The detail display region 520 includes an adjustment location display region 521, a coarse adjustment display region 522, and a fine adjustment display region 523.

In the adjustment location display region 521, an image of the vicinity of the operation location displayed in the reversed manner in the set value display region 510, and an arrow pointing at the operation location are displayed. In FIG. 6, an image of the vicinity of the sample aspiration position 1*a* in FIG. 2 is displayed in the adjustment location display region 521. Accordingly, the user can confirm the operation location targeted by position adjustment with reference to the image.

The coarse adjustment display region 522 includes a current value display region 522*a*, a preceding value display region 522*b*, and a preceding value button 522*c*. The current value display region 522*a* includes nine text boxes. In each text box, a corresponding set value displayed in the reversed manner in the set value display region 510 is displayed. The value displayed in a text box can be directly changed by the user. When the set value in a text box is changed, its corresponding set value in the set value display region 510 is also changed. It should be noted that the text box corresponding to a set value that does not define a moved position of the target unit is displayed in gray, and no input is allowed for the text box. For example, since ω, r, and y are not relevant to the sampler aspiration position displayed in the reversed manner, the text boxes in the current value display region 522*a* corresponding to ω, r, and y are displayed in gray as shown in FIG. 6.

In the preceding value display region 522*b*, values (preceding values) at the preceding adjustment of the respective set value items displayed in the reversed manner in the set value display region 510 are displayed. Such preceding values are read from the battery backup RAM 204 when display of the position adjustment main screen 500 is started, and are displayed in the preceding value display region 522*b*. When each set value is written in the battery backup RAM 204, its current value and its preceding value are written. It should be noted that, at the shipment, default values are written as the current value and the preceding value. When the preceding value button 522*c* is pressed, the preceding values displayed in the preceding value display region 522*b* are written in the text boxes in the current value display region 522*a*, respectively.

The fine adjustment display region 523 includes a fine adjustment button 523*a*. When the fine adjustment button 523*a* is pressed, the fine adjustment screen 600 (see FIG. 7) described later is displayed. That is, the user performs coarse adjustment of an operation position by inputting a specific numerical value in the coarse adjustment display region 522, and when the user wishes to perform fine adjustment, the user presses the fine adjustment button 523*a*.

A check box 524 is checked by the user when adjustment for the operation location displayed in the reversed manner in the set value display region 510 is completed. Accordingly, the color of the corresponding operation location item and set value items is changed. In FIG. 6, the color of the operation location "11: R1 reagent dispensing position" has been changed. Even when another operation location item is selected after the check box 524 is checked, the operation location item and set value items whose color has been changed will maintain the same color. Accordingly, the user can confirm the operation location on which position adjustment has been completed.

When the OK button 531 is pressed by the user, all the set values displayed in the set value display region 510 are stored in the battery backup RAM 204, and the position adjustment main screen 500 is closed. When the cancel button 532 is pressed by the user, all the set values displayed in the set value display region 510 are discarded, and the position adjustment main screen 500 is closed. Specifically, in the position adjustment main screen 500, set values changed in the coarse adjustment display region 522 and set values changed in the fine adjustment screen 600 described later are all temporarily stored in the RAM 403 of the control device 4. When the OK button 531 is pressed, the set values stored in the RAM 403 are written in the battery backup RAM 204, and when the cancel button 532 is pressed, the set values stored in the RAM 403 are discarded.

Figure 7:
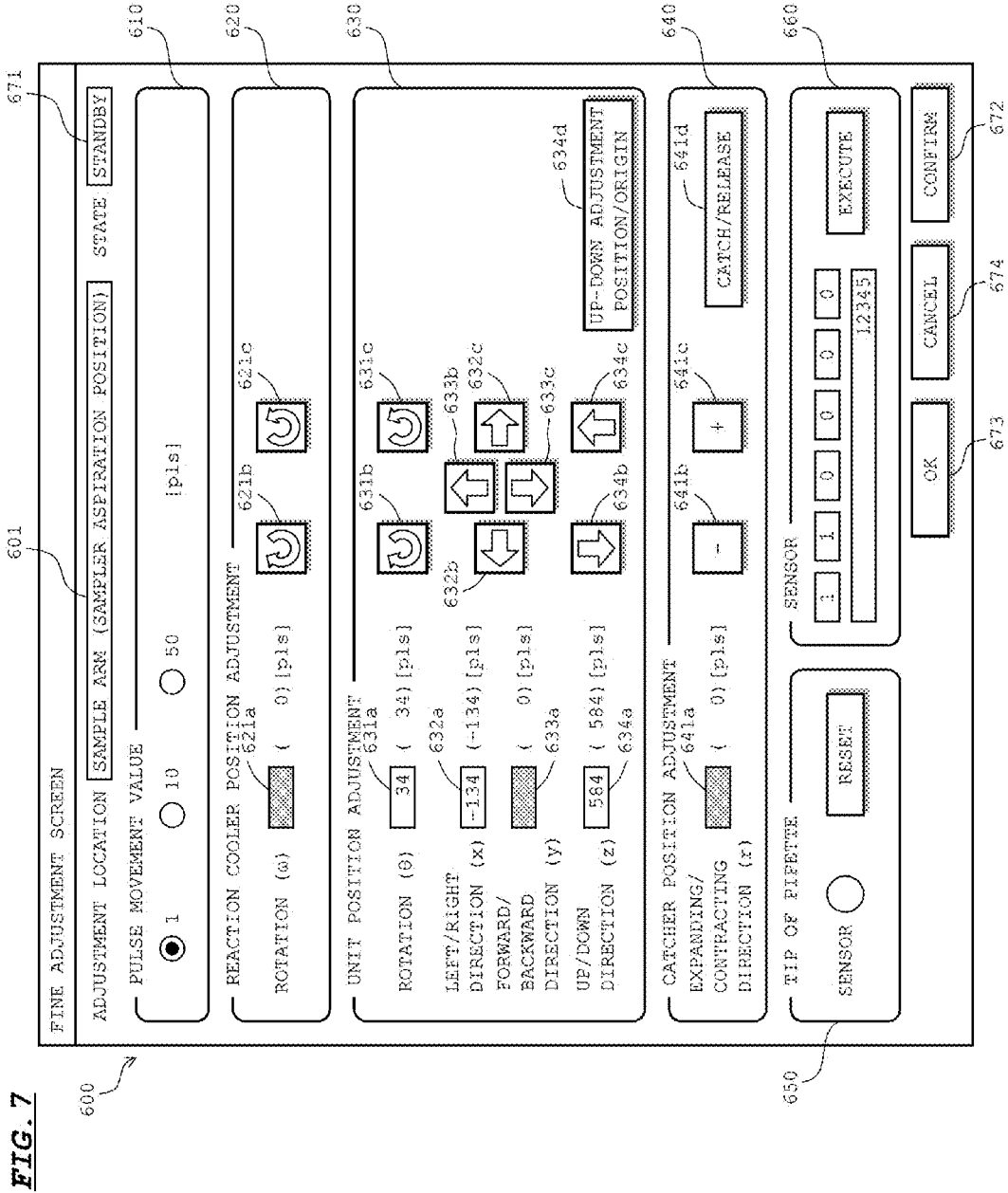
FIG. 7 shows a fine adjustment screen according to an embodiment.

FIG. 7 shows the fine adjustment screen 600. As in the case of the position adjustment main screen 500, the fine adjustment screen 600 is also displayed in a synchronized manner in the display input section 410 of the control device 4 and the display section 130 of the terminal device 100. Accordingly, the user can perform an operation onto the fine adjustment screen 600, via either the display input section 410 or the input section 120.

The fine adjustment screen 600 includes an adjustment location display region 601, a pulse movement value display region 610, a reaction cooler position adjustment display region 620, a unit position adjustment display region 630, a catcher position adjustment display region 640, a tip-of-pipette display region 650, a sensor display region 660, a state display region 671, a confirmation button 672, an OK button 673, and a cancel button 674.

In the adjustment location display region 601, a unit targeted by fine adjustment and an operation location of the unit are displayed. That is, the operation location displayed in the reversed manner in the set value display region 510 when the fine adjustment button 523*a* shown in FIG. 6 is pressed and the unit that includes the operation location are displayed in the adjustment location display region 601.

The pulse movement value display region 610 includes three selectable radio buttons. The number assigned to each radio button represents the number of pulses that drive the unit when one of movement buttons 621*b* 621*c*, 631*b* to 634*b*, 631*c* to 634*c*, 641*b*, and 641*c* described later is pressed once. The user can set a unit of movement to be used during fine adjustment, by selecting any one of the radio buttons.

When the fine adjustment button 523a in FIG. 6 is pressed and display is switched from the position adjustment main screen 500 to the fine adjustment screen 600, values of ω, θ, x, y, z, and r displayed in the current value display region 522a of the position adjustment main screen 500 are displayed in text labels 621a, 631a to 634a, and 641a, respectively. Simultaneously, the unit displayed in the reversed manner in the set value display region 510 of the position adjustment main screen 500 is driven from its origin position to the position defined by the values of ω, θ, x, and y displayed in the current value display region 522a. It should be noted that positions in the up/down direction and the expanding/contracting direction of the unit are not moved to the positions defined by the values of z and r. Positions in the up/down direction and the expanding/contracting direction are moved to the positions defined by the values of z and r, by pressing movement auxiliary buttons 634d and 641d described later. Accordingly, unintentional collision of the unit against another mechanism in the apparatus can be prevented.

When the movement button 621b or 621c of the reaction cooler position adjustment display region 620 is pressed once, the receiving-side mechanism corresponding to the unit displayed in the adjustment location display region 601 is rotated clockwise or counterclockwise, respectively, by the amount corresponding to the pulse movement value set in the pulse movement value display region 610. Associated with this, the value in the text label 621a is increased or decreased. In the example shown in FIG. 7, since the receiving-side mechanism (the sample transporting section 3) does not rotate about the Z axis at the sampler aspiration position (the sample aspiration position 1a in FIG. 2) being the adjustment location, the text label 621a is displayed in gray. In this case, even if the movement button 621b or 621c is pressed, no change is made in the receiving-side mechanism (the sample transporting section 3).

When the movement buttons 631b or 631c, the movement buttons 632b or 632c, the movement buttons 633b or 633c, or the movement buttons 634b or 634c in the unit position adjustment display region 630 is pressed once, the unit is moved clockwise, counterclockwise, rightward, leftward, forward, backward, downward, or upward, respectively, and associated with this, the corresponding value of the text labels 631a to 634a is increased or decreased. It should be noted that the movement buttons 634b and 634c become active when the movement auxiliary button 634d is pressed. In the example shown in FIG. 7, since the sample arm (the sample dispensing arm 5 in FIG. 2) being the adjustment target unit does not move in the Y axis direction (forward/backward direction) at the sampler aspiration position (the sample aspiration position 1a in FIG. 2) being the adjustment location, the text label 633a is displayed in gray. In this case, even if the movement button 633b or 633c is pressed, no change is made in the sample arm.

When the movement auxiliary button 634d is pressed by the user, the unit is positioned at the position in the up/down direction indicated in the text label 634a. When the movement auxiliary button 634d is pressed again, the unit is positioned at its origin position.

When the movement button 641b or 641c in the catcher position adjustment display region 640 is pressed, the unit is moved in the expanding/contracting direction, and associated with this, the value of the text label 641a is increased or decreased. It should be noted that the movement buttons 641b and 641c become active when the movement auxiliary button 641d is pressed. In the example shown in FIG. 7, since the sample arm (the sample dispensing arm 5 in FIG. 2) being the adjustment target unit does not expand or contract at the sampler aspiration position (the sample aspiration position 1a in FIG. 2) being the adjustment location, the text label 641a is displayed in gray. In this case, even if the movement button 641b or 641c is pressed, no change is made in the sample arm.

When the movement auxiliary button 641d is pressed by the user, the unit is expanded or contracted to the position shown in the text label 641a. When the movement auxiliary button 641d is pressed again, the unit is positioned at its origin position.

The tip-of-pipette display region 650 includes a circular region for indicating a detection signal of a sensor which detects that the tip of the pipette has been brought into contact with a liquid surface, and a button for resetting the indication of this region. The sensor display region 660 includes six regions for respectively indicating detection signals of sensors relating to the unit displayed in the adjustment location display region 601, a button for causing execution of reading a bar code when these sensors include a bar code reader, and a text label for displaying the value of the read bar code.

In the state display region 671, an operation state of the adjustment target unit is displayed. When the movement auxiliary buttons 634d and 641d, and the confirmation button 672 described later are pressed and the unit is being moved, "moving" is displayed in the state display region 671. When the unit is in a state where it can be adjusted, "standby" is displayed in the state display region 671.

When the confirmation button 672 is pressed, the unit displayed in the adjustment location display region 601 is returned to its origin position once, and then, the unit is moved to the adjustment location defined by ω, θ, x, y, z, and r. Accordingly, by viewing the unit being actually driven, the user can confirm whether the position adjustment performed via the fine adjustment screen 600 is appropriate.

When the OK button 673 is pressed, the fine adjustment screen 600 is closed, and the position adjustment main screen 500 in FIG. 6 is displayed. At this time, the set values that have been displayed in the text labels 621a, 631a to 634a, and 641a are reflected in the set value display region 510 of the position adjustment main screen 500 and in the current value display region 522a. When the cancel button 674 is pressed, the contents set on the fine adjustment screen 600 are discarded, and the fine adjustment screen 600 is closed.

Figure 8:
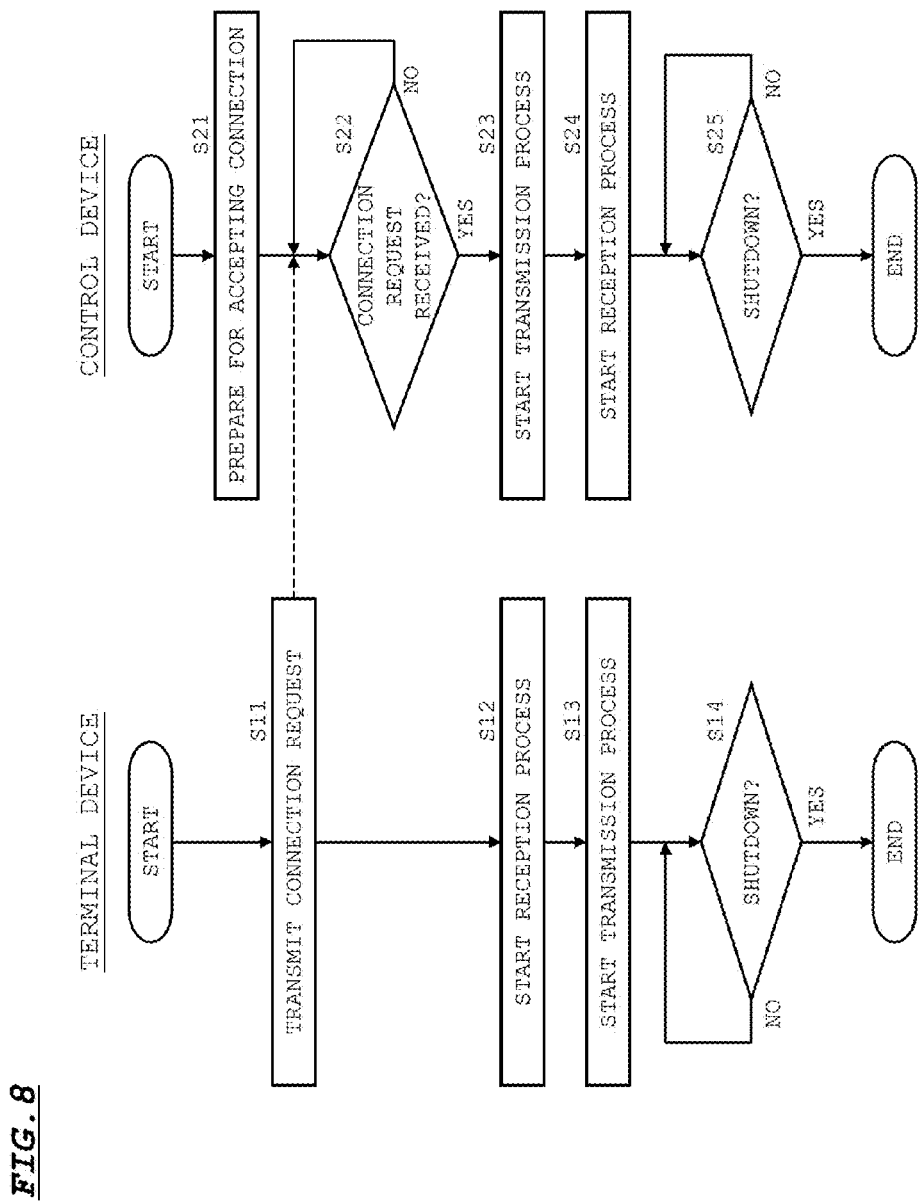
FIG. 8 shows a flow chart of processes performed by a terminal device and a control device according to an embodiment.

FIG. 8 shows a flow chart of processes performed by the terminal device 100 and the control device 4, respectively.

The CPU 111 of the terminal device 100 transmits a connection request to the control device 4 via the communication interface 118, first (S11). Specifically, the user designates an IP address of the control device 4 via the input section 120 of the terminal device 100, and inputs an instruction to try to establish communication with the control device 4. When the instruction is inputted, the communication interface 118 transmits an IP packet via the wireless LAN router (not shown) to the designated IP address. When a response to this is received from the control device 4, a wireless communication channel is established between the terminal device 100 and the control device 4. The communication between the terminal device 100 and the control device 4 thereafter is performed through transmission and reception of IP packets therebetween using a TCP/IP protocol.

Subsequently, the CPU 111 starts a reception process and a transmission process (S12, S13). In the reception process, the CPU 111 causes the display section 130 to display a screen based on data received from the control device 4. When an input is performed onto this screen, the CPU 111 transmits the inputted information to the control device 4 in the transmission process. The processes started at S12 and S13 are repeated until a shutdown instruction is issued (S14). The reception process and the transmission process of the terminal device 100 will be described later with reference to FIGS. 9A and 9B.

The CPU 401 of the control device 4 prepares for accepting connection from the terminal device 100, first (S21), and causes the processing to wait until receiving a connection request from the terminal device 100 (S22). Upon receiving the connection request from the terminal device 100 via the communication interface 408 (S22: YES), the CPU 401 transmits a response to this to the terminal device 100. As a result, a wireless communication channel is established between the terminal device 100 and the control device 4.

Subsequently, the CPU 401 starts a transmission process and a reception process (S23, S24). The CPU 401 transmits data to the terminal device 100 in the transmission process and receives, in the reception process, data transmitted from the terminal device 100. The processes stared at S23 and S24 are repeated until a shutdown instruction is issued (S25). The transmission process and the reception process of the control device 4 will be described later with reference to FIGS. 10A and 10B.

It should be noted that the reception process and the transmission process of the terminal device 100 and the reception process and the transmission process of the control device 4 are respectively performed in parallel with each other.

In the present embodiment, image data, information indicating a position (a coordinate position on the screen) and a region (the size of a region originating at the coordinate position) for displaying an image, and discernment information indicating whether the image data is for displaying an image of the entire screen or for displaying a part of the screen are transmitted from the control device 4 to the terminal device 100. The terminal device 100 displays an image based on the image data so as to fit in the designated region (size), at the designated position (coordinates). Further, information indicating an input position (a coordinate position on the screen) on the screen displayed on the terminal device 100 or an inputted content (key information) is transmitted from the terminal device 100 to the control device 4. Thus, in the present embodiment, it is sufficient that the terminal device 100 has a function of reproducing received image data as an image at the designated position and region, and a function of transmitting an input position (coordinate position) on the screen and an inputted content (key information). Such functions can be realized, for example, by installing a general-purpose program in the terminal device 100 as described above.

FIG. 9A is a flow chart showing the reception process performed by the terminal device 100.

Upon receiving data from the control device 4 (S101: YES), the CPU 111 of the terminal device 100 determines whether the received data includes image data of the entire screen or image data of a part of the screen (S102, S106). Such determination is performed based on the above-described discernment information included in the received data. When the received data includes neither image data of the entire screen nor image data of a part of the screen (S102: NO, S106: NO), the processing is returned to S101.

When the received data includes image data of the entire screen (S102: YES), the CPU 111 obtains information of the entire screen (image data and information regarding a display size of this image) from the received data (S103). It should be noted that image data transmitted from the control device 4 to the terminal device 100 is in a compressed format (e.g., PNG format) in order to reduce the file size. Subsequently, the CPU 111 expands the obtained screen data into a format used before the compression (S104), and displays the expanded image on the display section 130 in the designated size. Accordingly, the entire screen of the display section 130 is updated (S105).

On the other hand, when the received data includes image data of a part of the screen (S102: NO, S106: YES), the CPU 111 obtains update information (image data of the part of the screen, and the size of a region for displaying this image, and a coordinate position on the screen of this region) from the received data (S107). Subsequently, the CPU 111 expands the obtained image data into a format used before the compression (S108), and displays an image based on this image data in the region having the designated size at the designated coordinate position. Accordingly, the part of the screen of the display section 130 is updated (S109). For example, only the region corresponding to the text label 632a in FIG. 7 is updated. In this manner, the processes of S101 to 109 are repeated until a shutdown instruction is issued (S110).

FIG. 9B is a flow chart showing the transmission process performed by the terminal device 100.

When the screen displayed on the display section 130 is clicked via the input section 120 by the user (S111: YES), the CPU 111 of the terminal device 100 obtains coordinates of the clicked position (S112) and transmits click information including these coordinates to the control device 4 (S113). When a key input (input on a digit key or the like) is performed via the input section 120 by the user, the CPU 111 transmits to the control device 4 key information corresponding to the key on which the input has been performed (S115). In this manner, the processes of S111 to 115 are repeated until a shutdown instruction is issued (S116).

Figure 10B:
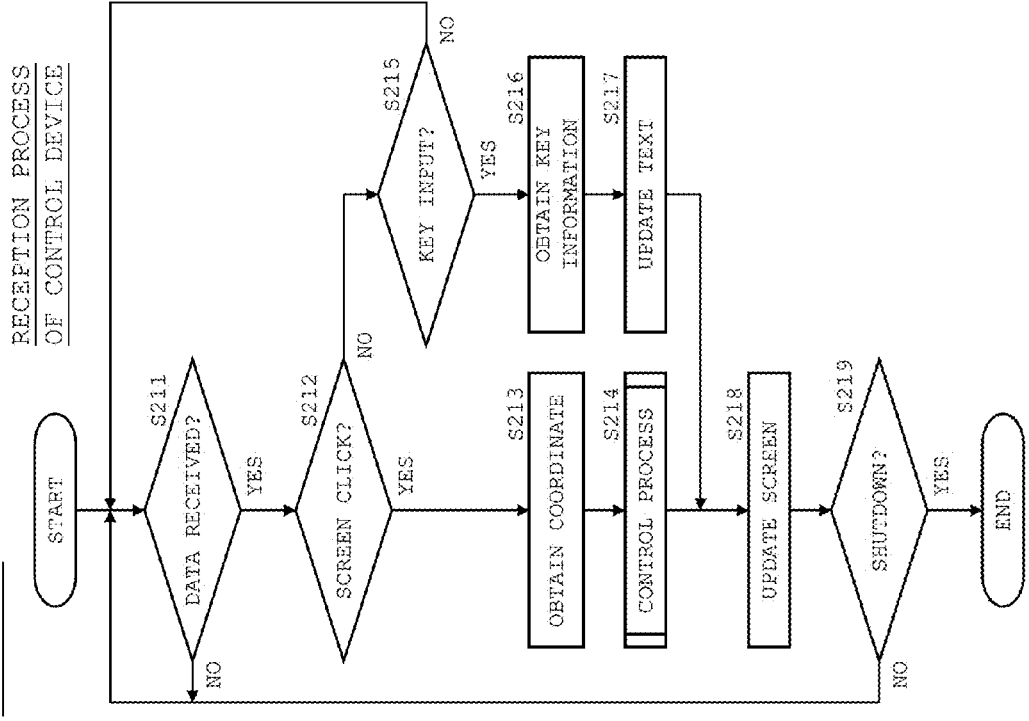
FIGS. 10A and 10B show flow charts of a transmission process and a reception process performed by a control device according to an embodiment.
Figure 10A:
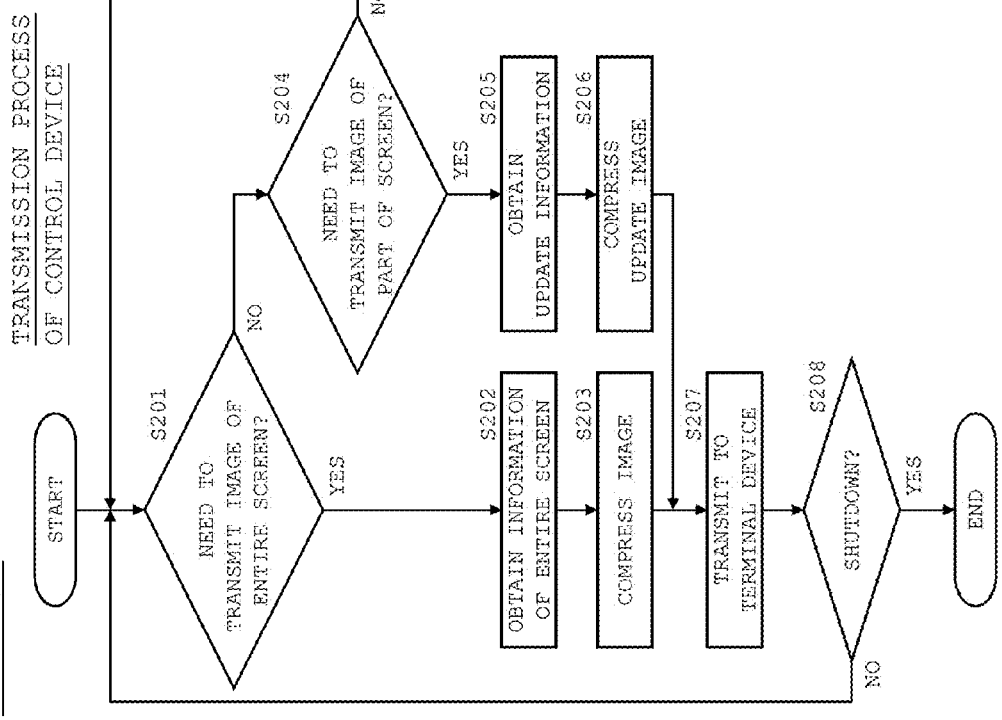

FIG. 10A is a flow chart showing the transmission process performed by the control device 4.

The CPU 401 of the control device 4 determines whether it is necessary to transmit image data of the entire screen (S201), and further determines whether it is necessary to transmit image data of a part of the screen (S204). When the transmission process is started at S23 in FIG. 8 and when the screen is switched between the position adjustment main screen 500 in FIG. and the fine adjustment screen 600 in FIG. 7, the CPU 401 determines that it is necessary to transmit image data of the entire screen (S201: YES). When the state of a part of the screen is changed due to an input performed onto the position adjustment main screen 500 or the fine adjustment screen 600, the CPU 401 determines that it is necessary to transmit image data of a part of the screen (S204: YES).

Upon determining that it is necessary to transmit an image of the entire screen (S201: YES), the CPU 401 obtains image data of the entire screen and a display size of this image (S202), and compresses the image data, among these, into a predetermined format (S203). On the other hand, upon determining that it is necessary to transmit image data of a part of the screen (S201: NO, S204: YES), the CPU 401 obtains image data of a region (hereinafter referred to as a "change region") corresponding to the changed portion in the screen, the size of the change region, and the coordinate position on the screen of the change region (S205), and compresses the image data, among these, into a predetermined format (S206).

Subsequently, the CPU 401 transmits, to the terminal device 100, information of the entire screen including the image data compressed in S203 and the display size of the image, or update information including the image data compressed in S206 and the size and the coordinate position of the change region (S207). Here, each of the information of the entire screen and the update information further includes discernment information indicating whether the image data is data regarding an image of the entire screen or regarding an image of a part of the screen. The processes of S201 to S207 are repeated until a shutdown instruction is issued (S208).

FIG. 10B is a flow chart showing the reception process performed by the control device 4.

Upon receiving data from the terminal device 100 (S211: YES), the CPU 401 of the control device 4 determines whether the received data is data regarding a screen click or a key input (S212, S215). When the received data is data regarding neither a screen click nor a key input (S212: NO, S215: NO), the processing is returned to S211.

When the received data is data regarding a screen click (S212: YES), that is, the received data is the data transmitted in S113 in FIG. 9B, the CPU 401 obtains coordinates included in this data (S213). Subsequently, based on the obtained coordinates, the CPU 401 performs a "control process" (S214). The control process will be described later with reference to FIGS. 11 and 12.

On the other hand, when the received data is data regarding a key input (S212: NO, S215: YES), that is, the received data is data transmitted in S115 in FIG. 9B, the CPU 401 obtains key information included in this data (S216). Subsequently, based on this key information, the CPU 401 updates the text displayed in the display input section 410 (S217). Typically, at the timing when key information is received, a region into which text can be inputted, such as a text box on the screen, has been focused as a result of a click made onto the screen therebefore. In S217, based on the obtained information, the CPU 401 updates the display in such a focused region. When a region into which text can be inputted has not been focused at the timing of the process of S217, the CPU 401 invalidates the obtained text information.

When the state of the screen is changed as a result of the control process in S214 or the text update process in S217, the CPU 401 updates the screen (the position adjustment main screen 500 or the fine adjustment screen 600) on the display input section 410, accordingly (S218). It should be noted that, when the screen is thus updated, the determination in S201 or S204 in FIG. 10A becomes YES, and information for updating the screen is transmitted to the terminal device 100. Accordingly, the screen on the display input section 410 and the screen on the display section 130 on the terminal device 100 side are updated in a synchronized manner. In this manner, the processes of S211 to S218 are repeated until a shutdown instruction is issued (S219).

Figure 11:
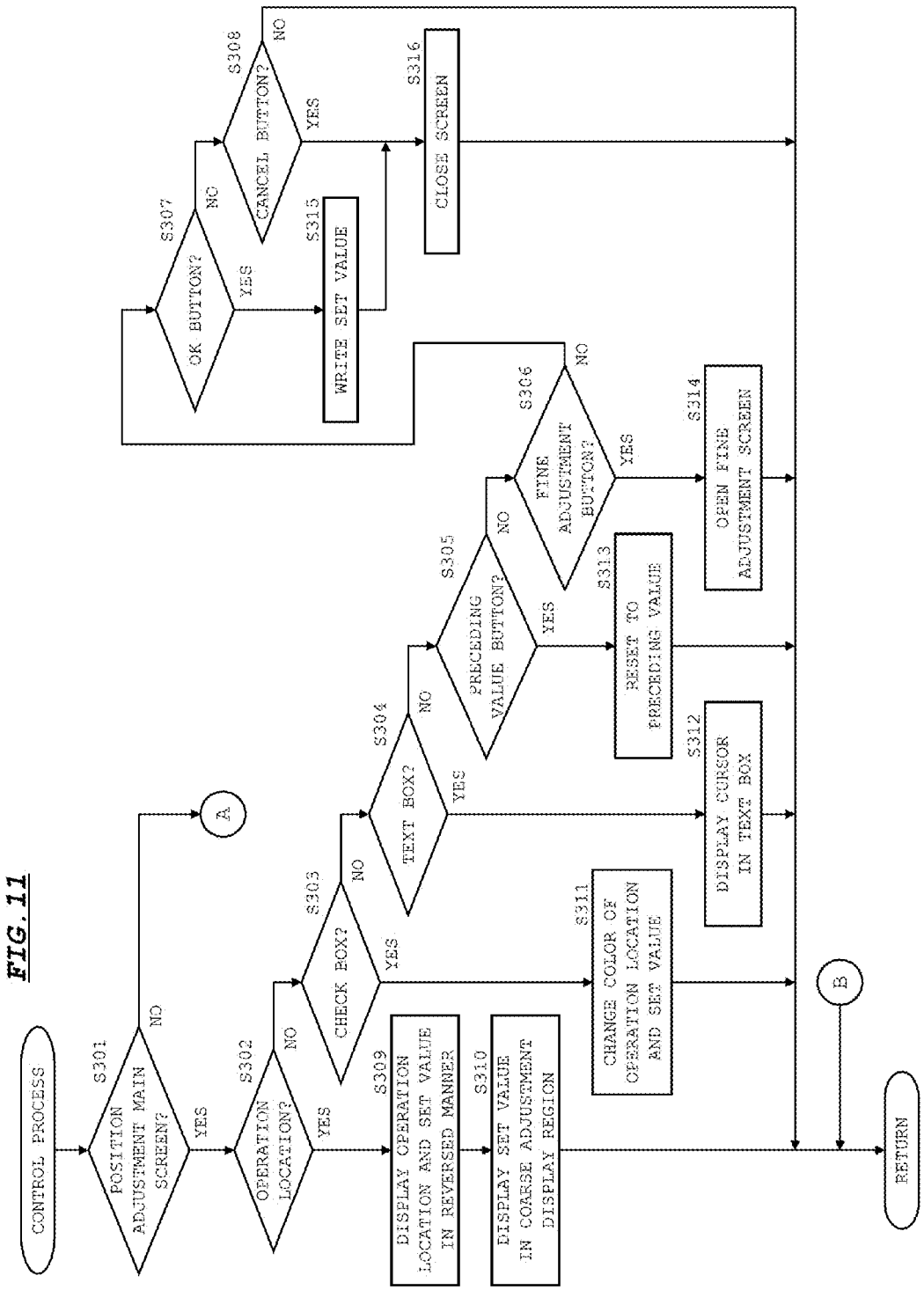
FIG. 11 is a flow chart showing major processes of the control process according to an embodiment.

FIG. 11 is a flow chart showing major processes of S214 (the control process) in FIG. 10B.

The CPU 401 of the control device 4 determines whether the screen determined as having been clicked in S212 in FIG. 10B is the position adjustment main screen 500 (S301). When this screen is not the position adjustment main screen 500 (S301: NO), that is, this screen is the fine adjustment screen 600, the processing is advanced to a terminal A. When the clicked screen is the position adjustment main screen 500 (S301: YES), the CPU 401 performs the following processes based on the coordinates (place clicked by the user) obtained in S213 in FIG. 10B.

When the clicked place is an operation location item in the set value display region 510 (S302: YES), the CPU 401 causes the items of the set values of this operation location to be displayed in a reversed manner (S309), and causes the set values of the clicked operation location to be displayed in the coarse adjustment display region 522 (S310). That is, in the current value display region 522a, the set values in the set value display region 510 are displayed, and in the preceding value display region 522b, the set values of this operation location at the time when the position adjustment main screen 500 was displayed are displayed.

When the clicked place is the check box 524 (S302: NO, S303: YES), the CPU 401 changes the color of the items of the operation location and the set values, in the set value display region 510, which correspond to the display in the detail display region 520 (S311). It should be noted that, when nothing is displayed in the detail display region 520 as in the case where the position adjustment main screen 500 is opened for the first time, the determination in S303 is NO even if the check box 524 is clicked.

When the clicked place is a text box in the current value display region 522a (S302 to S303: NO, S304: YES), the CPU 401 displays a cursor in the text box at the clicked place (S312).

When the clicked place is the preceding value button 522c (S302 to S304: NO, S305: YES), the CPU 401 replaces the values in the text boxes in the current value display region 522a with the corresponding values in the preceding value display region 522b (S313).

When the clicked place is the fine adjustment button 523a (S302 to S305: NO, S306: YES), the CPU 401 opens the fine adjustment screen 600 (S314).

When the clicked place is the OK button 531 (S302 to S306: NO, S307: YES), the CPU 401 writes the set values displayed in the set value display region 510 into the battery backup RAM 204 (S315). Subsequently, the CPU 401 closes the position adjustment main screen 500 (S316).

When the clicked place is the cancel button 532 (S302 to S307: NO, S308: YES), the CPU 401 closes the position adjustment main screen 500 (S316).

The clicked place is none of the above regions (S302 to S308: NO), the processes are not performed and the control process ends.

It should be noted that, when the state of the screen is changed as a result of any of S309 to S314 and S316, the CPU 401 updates, in the process step of S218 in FIG. 10B, the screen (the position adjustment main screen 500 or the fine adjustment screen 600) on the display input section 410, in accordance with the update content of the corresponding one of S309 to S314 and S316. When the screen is updated in this manner, the determination in S201 or S204 in FIG. 10A becomes YES, and information for updating the screen is transmitted from the control device 4 to the terminal device 100. Accordingly, the screen on the display input section 410 of the control device 4 and the screen on the display section 130 on the terminal device 100 side are updated in a synchronized manner.

Figure 12:
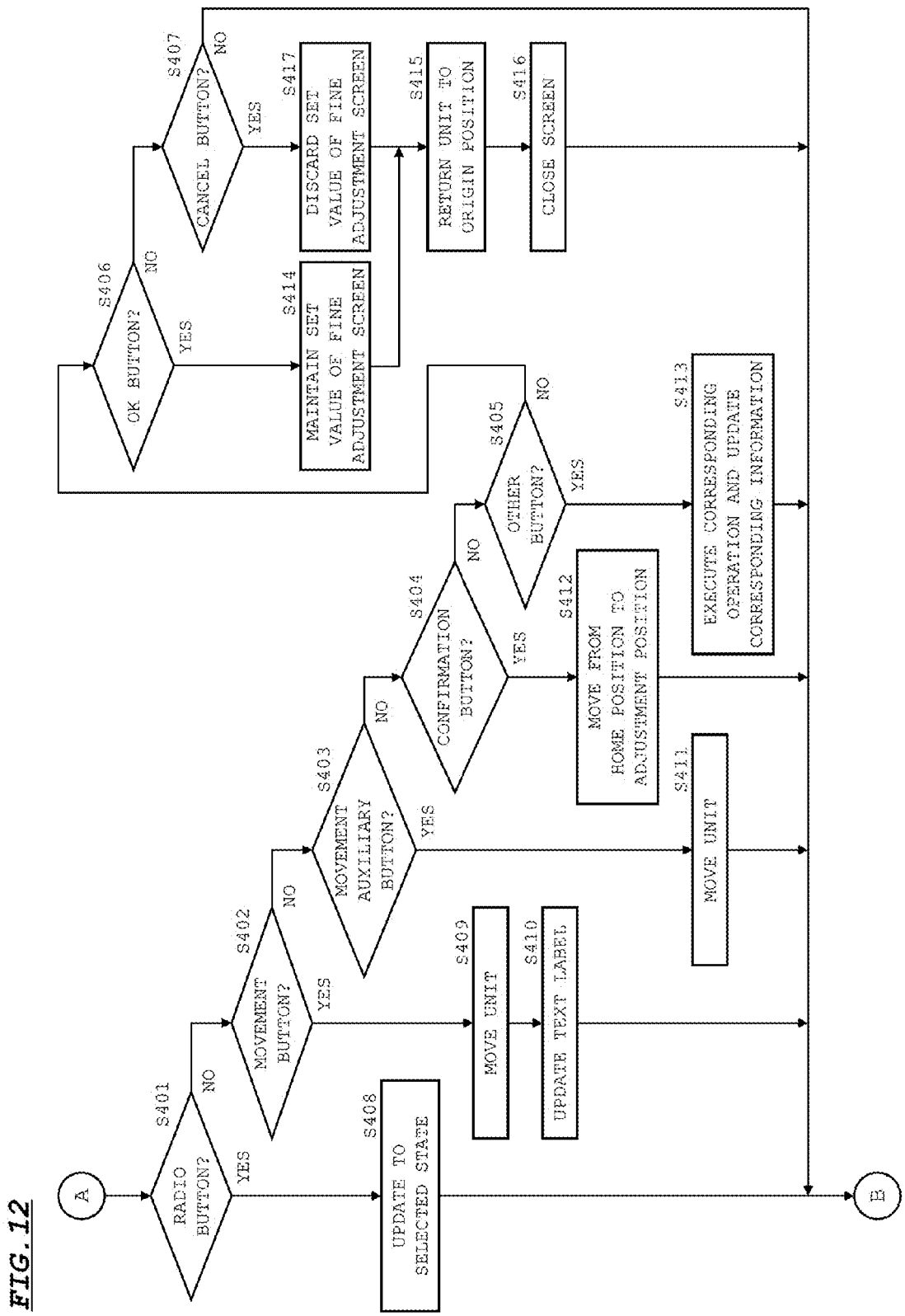
FIG. 12 is a flow chart showing major processes of the control process according to an embodiment.

FIG. 12 is a flow chart showing major processes after the terminal A in FIG. 11.

With respect to the fine adjustment screen 600, the CPU 401 of the control device 4 performs the following processes, based on the coordinates (the place clicked by the user) obtained in S213 in FIG. 10B.

When the clicked place is a radio button in the pulse movement value display region 610 (S401: YES), the CPU 401 updates the radio button at the clicked place to a selected state (S408). Simultaneously, the CPU 401 sets the unit of movement used when a movement button is pressed, to the number of pulses corresponding to the selected radio button.

When the clicked place is any one of the movement buttons 621b, 621c, 631b to 634b, 631c to 634c, 641b, and 641c (S401: NO, S402: YES), the CPU 401 moves the unit displayed in the adjustment location display region 601 (S409). At this time, drive pulses are outputted by the number of pulses selected in the pulse movement value display region 610, to a corresponding stepping motor in the stepping motor section 211. Subsequently, the CPU 401 updates the one of the text labels 621a, 631a to 634a, and 641a that corresponds to the drive, in accordance with the drive amount (S410). When the clicked place is a movement button that corresponds to a text label displayed in gray, the determination in S402 is NO.

When the clicked place is either the movement auxiliary button 634d or 641d (S401 to S402: NO, S403: YES), the CPU 401 moves the unit as described above (S411).

When the clicked place is the confirmation button 672 (S401 to S403: NO, S404: YES), the CPU 401 moves the unit from its origin position to the adjustment location as described above (S412).

When the clicked place is a button other than the above (the button in the tip-of-pipette display region 650 or the button in the sensor display region 660) (S401 to S404: N0, S405: YES), the CPU 401 performs the corresponding operation and updates the corresponding information (S413).

When the clicked place is the OK button 673 (S401 to S405: NO, S406: YES), the CPU 401 maintains the set values displayed in the fine adjustment screen 600 (S414). Subsequently, the CPU 401 returns the unit displayed in the adjustment location display region 601 to its origin position (S415), and closes the fine adjustment screen 600 (S416).

When the clicked place is the cancel button 674 (S401 to S406: NO, S407: YES), the CPU 401 discards the set values displayed in the fine adjustment screen 600 (S417). Subsequently, the CPU 401 returns the unit displayed in the adjustment location display region 601 to its origin position (S415), and closes the fine adjustment screen 600 (S416).

When the clicked place is none of the above regions (S401 to S407: NO), the processes are not performed and the processing is advanced to a terminal B, and the control process ends.

It should be noted that, when the state of the screen is changed as a result of S408, S410, S413 or S416, the CPU 401 updates, in the process step of S218 in FIG. 10B, the screen (the position adjustment main screen 500 or the fine adjustment screen 600) on the display input section 410, in accordance with the update content of the corresponding one of S408, S410, S413, and S416. When the screen is updated in this manner, the determination in S201 or S204 in FIG. 10A becomes YES, and information for updating the screen is transmitted from the control device 4 to the terminal device 100. Accordingly, the screen on the display input section 410 of the control device 4 and the screen on the display section 130 on the terminal device 100 side are updated in a synchronized manner.

In the flow charts in FIG. 10B and FIGS. 11 and 12, adjustment of the unit or update of the screen are performed through an input onto the screen displayed in the display section 130 of the terminal device 100. However, also in the case where adjustment of the unit and update of the screen are performed through an input onto the screen displayed in the display input section 410 on the control device 4 side, similar processes are performed.

In this case, S211 is omitted from the flow chart in FIG. 10B, and in S212 and S215, it is determined whether a click and a key input have been performed on the screen displayed in the display input section 410, respectively. Further, in S213 and S216, based on the input onto the display input section 410, coordinates of the clicked position and key information are obtained. The other processes are the same as those in the above embodiment. Also in this case, in accordance with the update of the screen on the display input section 410, the determination in S201 or S204 in FIG. 10A becomes YES, and information for updating the screen is transmitted from the control device 4 to the terminal device 100. Accordingly, the screen on the display input section 410 of the control device 4 and the screen on the display section 130 on the terminal device 100 side are updated in a synchronized manner.

As described above, according to the present embodiment, even when the unit on which to perform position adjustment is away from the control device 4, by bringing the terminal device 100 near the unit, it is possible to give instruction to change set values of the unit via the position adjustment main screen 500 and the fine adjustment screen 600 displayed on the terminal device 100, while viewing the position of the unit. Therefore, when performing position adjustment of the unit, the user need not come and go between the position at which to operate the control device 4 and the unit, and can perform position adjustment of the unit very simply.

Further, according to the present embodiment, the screen on the display section 130 is displayed based on the data regarding the screen transmitted from the control device 4, and the information inputted via the input section 120 is transmitted to the control device 4. Moreover, a program for realizing such functions is installed in the terminal device 100. Therefore, the terminal device 100 need not have a special application for position adjustment installed therein, and thus, the terminal device 100 can be configured using a general-purpose computer and a general-purpose application. Accordingly, the terminal device 100 can be configured at a low cost and in a simple manner.

Further, according to the present embodiment, as shown in FIG. 10A, when the state of a part of the screen is changed, not image data of the entire screen but image data of the part of the screen is transmitted from the control device 4 to the terminal device 100. Accordingly, the amount of data to be transmitted to the terminal device 100 can be reduced.

Further, according to the present embodiment, by pressing an operation location item in the set value display region 510, the user can select a unit on which to perform position adjustment. In this case, in the adjustment location display region 521, an image of the vicinity of the operation location of the selected unit, and an arrow indicating the operation location are shown. Accordingly, the user can confirm at a glance where the unit on which to perform position adjustment is located.

Further, according to the present embodiment, an adjustment position of the unit can be set to a predetermined position via the coarse adjustment display region 522 of the position adjustment main screen 500 in a simple manner. Further, when a movement button is pressed on the fine adjustment screen 600, the adjustment position of the unit can be finely set. In addition, when performing setting using a movement button, the unit actually moves in accordance with the movement button. Therefore, the user can perform an appropriate position adjustment while confirming the moved position of the unit.

Further, according to the present embodiment, when the confirmation button 672 is pressed, the adjustment target unit is moved from its origin position to the position defined by set values. Accordingly, the user can confirm whether the set values that have been set are appropriate, while viewing the unit being driven.

An embodiment of the present invention has been described. However, the embodiment of the present invention is not limited to the above embodiment.

For example, in the above embodiment, a subject to be measured is exemplified by blood, but a subject to be measured may be urine. That is, the present invention can be applied to a specimen analyzer which tests urine, and further, the present invention can be applied to a clinical sample testing apparatus which tests other clinical samples.

Further, in the above embodiment, the set values of each unit in the measurement mechanism section 2 are stored in the battery backup RAM 204. However, the present invention is not limited thereto. The set values may be stored in the hard disk 404 of the control device 4 or the hard disk 114 of the terminal device 100.

Further, in the above embodiment, screen data generated in the control device 4 is transmitted to the terminal device 100. However, the present invention is not limited thereto. The terminal device 100 may generate screen data, and the screen data generated in the terminal device 100 may be transmitted to the control device 4. As a still another embodiment, the same application program as that installed in the control device 4 is installed in the terminal device 100, and an instruction of position adjustment may be issued from the terminal device 100 to the measurement mechanism section 2, not via the control device 4. In this case, in order to prevent an unintended operation from being performed due to an erroneous input in the terminal device 100, it is preferable that, in the terminal device 100, only the function that issues an instruction of position adjustment is set to be active, and the other functions are set to be inactive.

Further, in the above embodiment, in order to perform position adjustment of each unit in the measurement mechanism section 2, two screens, i.e., the position adjustment main screen 500 and the fine adjustment screen 600, are used. However, the present invention is not limited thereto. Only one screen may be used, or three or more screens may be used. For example, components of the position adjustment main screen 500 and the fine adjustment screen 600 may be arranged on one screen. Further, another screen on which only the coarse adjustment display region 522 of the position adjustment main screen 500 is displayed may be separately prepared.

Further, in the above embodiment, a notebook personal computer is used as the terminal device 100 of a portable type. However, the present invention is not limited thereto. Any terminal device that can be carried by a person may be used as the terminal device 100. For example, a personal digital assistance (PDA) or a smart phone may be used. Further, the terminal device 100 and the control device 4 are communicably connected to each other through wireless connection. However, the present invention is not limited thereto. The terminal device 100 and the control device 4 may be communicably connected to each other through wired connection. Wired communication may be realized, for example, by connecting the control device 4 and the terminal device 100 to each other with a LAN cable and using a TCP/IP protocol. As the LAN cable, a straight cable may be used to connect the control device 4 and the terminal device 100 via a hub, or a cross cable may be used to directly connect them.

Further, in the above embodiment, in order to display image data transmitted from the control device 4 and to transmit an inputted content to the control device 4, an application executed on AIR of Adobe Systems Incorporated is installed in the hard disk 114 of the terminal device 100. However, the present invention is not limited thereto. It is sufficient that a program that allows the control device 4 and the terminal device 100 to display the same screen in a synchronized manner is installed. For example, "pcAnywhere" of Symantec Corporation or "Remote Desktop" of Microsoft Corporation may be used.

In addition to the above, various modifications can be made as appropriate without departing from the scope of the technical idea defined by the claims.

What is claimed is:

1. A position adjustment method for a movable unit in a sample analyzer which includes: a first display section configured to display a position adjustment screen on which a numerical value for defining an operation position of the movable unit is entered or altered; a measurement section having a plurality of movable units each comprising a stepping motor and configured to perform a measurement of a sample by causing the movable unit to move to and function at the operation position defined with a numerical value entered or altered on the position adjustment screen by applying an amount of pulse signals proportional to the numerical value to the stepping motor; a control device; and a communication section configured to communicate with outside, the position adjustment method executed by the control device comprising:

receiving a connection request from a portable terminal device, held by an operator by hand, that comprises: a communication interface for performing wireless communication with the communication section; and a second display section different from the first display section;

establishing a wireless communication channel between the portable terminal device held by the operator by hand and the control device;

transmitting data for displaying the position adjustment screen to the portable terminal device held by the operator by hand;

causing the portable terminal device held by the operator by hand to display, on the second display section, the position adjustment screen on which a numerical value for defining the operation position of the movable unit is entered or altered based on the data, the position adjustment screen configured to enable the operator to select one of a plurality of operation positions, each of which at least one of the plurality of movable units is movable to, and to enter or alter a numerical value to define the selected operation position;

causing the portable terminal device to accept a selection of one of the plurality of operation positions on the position adjustment screen by the operator;

responsive to the selection of one of the plurality of operation positions, causing the portable terminal device to display, on the position adjustment screen displayed on the second display section, an image showing an operation position corresponding to the selected operation position and a numerical value of the selected operation position of previous setting, which is stored in and read out from a storage of the control device, the image guiding the operator holding the portable terminal device to the vicinity of the selected operation position to enable the operator to visually confirm any change in the operation position;
causing the portable terminal device to accept, on the position adjustment screen displayed on the second display section, a numerical value entered or altered by the operator for changing the numerical value of the selected operation position;
causing the measurement section of the sample analyzer to move the movable unit from an origin position to the operation position defined with the numerical value on the position adjustment screen by applying an amount of pulse signals proportional to the numerical value entered or altered on the position adjustment screen to the corresponding stepping motor; and
overwriting, at the control device, the numerical value of previous setting in the storage with the numerical value entered or altered on the position adjustment screen.

2. The position adjustment method for the movable unit in the sample analyzer according to claim 1, further comprising:
displaying the position adjustment screen based on the numerical values stored in the storage, on the first display section.

3. The position adjustment method for the movable unit in the sample analyzer according to claim 2, wherein
displaying the position adjustment screen based on the numerical values stored in the storage comprises updating the position adjustment screen displayed in the first display section in accordance with the numerical value entered or altered through the second display section, and
causing the portable terminal device to display the position adjustment screen comprises updating the position adjustment screen displayed in the second display section of the terminal device such that, in synchronization with the update of the position adjustment screen displayed in the first display section, the updated position adjustment screen is also displayed in the second display section of the terminal device.

4. The position adjustment method for the movable unit in the sample analyzer according to claim 3, wherein
updating the position adjustment screen comprises upon accepting a change of the numerical value through the second display section, generating a partial visual data of a region in which the changed numerical value is displayed, the region being a part of the position adjustment screen, and transmitting to the terminal device the generated partial visual data along with data designating a region to be changed.

5. The position adjustment method for the movable unit in the sample analyzer according to claim 1, wherein
the position adjustment screen includes a movement key for moving the movable unit by a predetermined movement amount, and
the measurement section moves the movable unit by the predetermined movement amount, every time the movement key in the position adjustment screen displayed in the terminal device is pressed.

6. The position adjustment method for the movable unit in the sample analyzer according to claim 1, wherein
the terminal device comprises a first wireless local area network card for performing wireless communication with the communication section and the communication section comprises a second wireless local area network card for performing wireless communication with the terminal device.

7. The position adjustment method for the movable unit in the sample analyzer according to claim 1, wherein
the position adjustment screen includes a button for accepting an instruction to display a fine adjustment screen,
the method further comprises upon accepting the instruction, displaying the fine adjustment screen including a movement key for moving the one of the plurality of movable units by a predetermined movement amount, and
moving the one of the plurality of movable units by the predetermined movement amount according to the operation of the movement key.

8. The position adjustment method for the movable unit in the sample analyzer according to claim 1, wherein the portable terminal device comprises one of: a notebook personal computer, a personal digital assistant, and a smart phone.

9. The position adjustment method for the movable unit in the sample analyzer according to claim 1, wherein the position adjustment screen displays an image showing an operation position corresponding to the selected operation position.

10. A sample analyzing system comprising:
a sample analyzer; and
a portable terminal device that is able to be carried by an operator by hand, independently of the sample analyzer and comprises a first wireless communication module and a first display section, wherein
the sample analyzer comprises:
a second display section, different from the first display section, configured to display a position adjustment screen on which a numerical value for defining an operation position of a movable unit is entered or altered;
a measurement section having a plurality of movable units each comprising a stepping motor and configured to perform a measurement of a sample by causing the movable unit to move to and function at an operation position defined with a numerical value entered or altered on the position adjustment screen by applying an amount of pulse signals proportional to the numerical value to the stepping motor;
a communication section configured to communicate with outside and comprising a second wireless communication module for performing wireless communication with the first wireless communication module of the portable terminal device; and
a controller configured to:
receive a connection request via the communication section from the portable terminal device held by the operator by hand;
establish a wireless communication channel between the first and second wireless communication modules;
transmit data for displaying the position adjustment screen to the portable terminal device held by the operator by hand via the wireless communication channel;
cause the portable terminal device held by the operator by hand, based on the data to display, on the first display section, the position adjustment screen on which a numerical value for defining the operation position of the movable unit is entered or altered, the position adjustment screen configured to enable the operator to select one of a plurality of operation positions, each of which at least one of the plurality of movable units is movable to, and to enter or alter a numerical value to define the selected operation position;

cause the portable terminal device held by the operator to accept a selection of one of the plurality of operation positions by the operator via the position adjustment screen displayed on the first display section;

cause the portable terminal device held by the operator, responsive to the selection of one of the plurality of operation positions, to display an image showing an operation position corresponding to the selected operation position, and display a numerical value of the selected operation position of previous setting, which is stored in and read out from a storage of the controller, on the position adjustment screen displayed on the first display section, the image guiding the operator holding the portable terminal device to the vicinity of the selected operation position to enable the operator to visually confirm any change in the selected operation position;

cause the portable terminal device held by the operator to accept a numerical value entered or altered for changing the numerical value of the selected operation position via the position adjustment screen displayed on the first display section;

receive the changed numerical value from the portable terminal device via the wireless communication channel, responsive to the numerical value entered or altered;

cause the measurement section to move the movable unit from an origin position to the operation position defined with the numerical value on the position adjustment screen by applying an amount of pulse signals proportional to the numerical value entered or altered on the position adjustment screen to the corresponding stepping motor; and overwriting the numerical value of previous setting in the storage with the numerical value entered or altered on the position adjustment screen.

11. The sample analyzing system according to claim 10, wherein
the controller causes the second display section to display the position adjustment screen based on the numerical values stored in the storage.

12. The sample analyzing system according to claim 11, wherein the controller
updates the position adjustment screen displayed in the second display section in accordance with the numerical value entered or altered through the second display section, and updates the position adjustment screen displayed in the first display section of the terminal device such that, in synchronization with the update of the position adjustment screen displayed in the second display section, the updated position adjustment screen is also displayed in the first display section of the terminal device.

13. The sample analyzing system according to claim 12, wherein
upon accepting the change of the numerical value, the controller generates a partial visual data of a region in which the changed numerical value is displayed, the region being a part of the position adjustment screen, and wirelessly transmits to the terminal device the generated image data along with data designating a region to be changed.

14. The sample analyzing system according to claim 10, wherein
the position adjustment screen includes a movement key for moving the one of the plurality of movable units by a predetermined movement amount, and
the controller moves the one of the plurality of movable units by the predetermined movement amount, every time the movement key in the position adjustment screen displayed in the terminal device is pressed.

15. The sample analyzing system according to claim 10, wherein
the portable terminal device comprises a first wireless local area network card as the first wireless communication module for and the communication section comprises a second wireless local area network card as the second wireless communication module.

16. The sample analyzing system according to claim 10, wherein
the position adjustment screen includes a button for accepting an instruction to display a fine adjustment screen,
the portable terminal device displays the fine adjustment screen including a movement key for moving the one of the plurality of movable units by a predetermined movement amount according to an operation of the button, and
the measurement section moves the one of the plurality of movable units by the predetermined movement amount according to the operation of the movement key.

17. The sample analyzing system according to claim 10, wherein the portable terminal device comprises one of: a notebook personal computer, a personal digital assistant, and a smart phone.

18. The sample analyzing system according to claim 10, wherein the position adjustment screen displays an image showing an operation position corresponding to the selected operation position.

* * * * *